(12) United States Patent
Ji et al.

(10) Patent No.: US 10,888,296 B2
(45) Date of Patent: Jan. 12, 2021

(54) METHODS AND SYSTEMS FOR MODULATING RADIATION DOSE

(71) Applicant: SHANGHAI UNITED IMAGING HEALTHCARE CO., LTD., Shanghai (CN)

(72) Inventors: Min Ji, Shanghai (CN); Weili Peng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 93 days.

(21) Appl. No.: 16/029,707

(22) Filed: Jul. 9, 2018

(65) Prior Publication Data

US 2020/0000425 A1    Jan. 2, 2020

(30) Foreign Application Priority Data

Jun. 29, 2018 (CN) .......................... 2018 1 0697936
Jun. 29, 2018 (CN) .......................... 2018 1 0715092
Jun. 29, 2018 (CN) .......................... 2018 1 0715382

(51) Int. Cl.
  *A61B 6/00* (2006.01)
  *G06K 9/46* (2006.01)
  (Continued)

(52) U.S. Cl.
  CPC ................ *A61B 6/544* (2013.01); *A61B 6/03* (2013.01); *A61B 6/488* (2013.01); *G06K 9/46* (2013.01);
  (Continued)

(58) Field of Classification Search
  CPC .......... A61B 6/03; A61B 6/544; A61B 5/7228
  See application file for complete search history.

(56) References Cited

U.S. PATENT DOCUMENTS

2017/0095223 A1* 4/2017 Tian ........................ G06F 19/00
2018/0040121 A1* 2/2018 Lin ......................... A61B 6/032
(Continued)

FOREIGN PATENT DOCUMENTS

| CN | 102063728 A | 5/2011 |
| CN | 104851768 A | 8/2015 |
| CN | 107928694 A | 4/2018 |

OTHER PUBLICATIONS

First Office Action in Chinese Application No. 201810715382.4 dated Aug. 12, 2020, 16 pages.

*Primary Examiner* — Wen W Huang
(74) *Attorney, Agent, or Firm* — Metis IP LLC

(57) ABSTRACT

A method and system for determining a dose of modulation (DOM) profile are provided. The method may include obtaining a 3D image and a topogram image of the object. The method may further include obtaining a dose of modulation (DOM) profile generation model. The DOM profile generation model may be generated by training a preliminary model based on a plurality of sample CT images, a plurality of sample 3D images corresponding to the plurality of sample CT images, respectively, and a plurality of sample topogram images corresponding to the plurality of sample CT images, respectively. The method may further include executing the DOM profile generation model to generate a DOM profile related to a computed tomography (CT) scan of the object based on the 3D image and the topogram image of the object.

9 Claims, 15 Drawing Sheets

(51) Int. Cl.
*G06T 7/60* (2017.01)
*G06T 7/11* (2017.01)
*G06K 9/62* (2006.01)
*G06T 7/13* (2017.01)
*A61B 6/03* (2006.01)

(52) U.S. Cl.
CPC .............. *G06K 9/6257* (2013.01); *G06T 7/11* (2017.01); *G06T 7/13* (2017.01); *G06T 7/60* (2013.01); *G06K 2209/05* (2013.01); *G06T 2207/10028* (2013.01); *G06T 2207/10081* (2013.01); *G06T 2207/20081* (2013.01); *G06T 2207/20084* (2013.01)

(56) References Cited

U.S. PATENT DOCUMENTS

| | | | | |
|---|---|---|---|---|
| 2018/0228460 A1* | 8/2018 | Singh | .................... | A61B 6/5217 |
| 2018/0360399 A1* | 12/2018 | Pasquier | ................. | A61B 6/405 |
| 2018/0360402 A1* | 12/2018 | Carmi | ....................... | G06T 7/13 |
| 2019/0099148 A1* | 4/2019 | Rupcich | ................. | A61B 6/488 |

\* cited by examiner

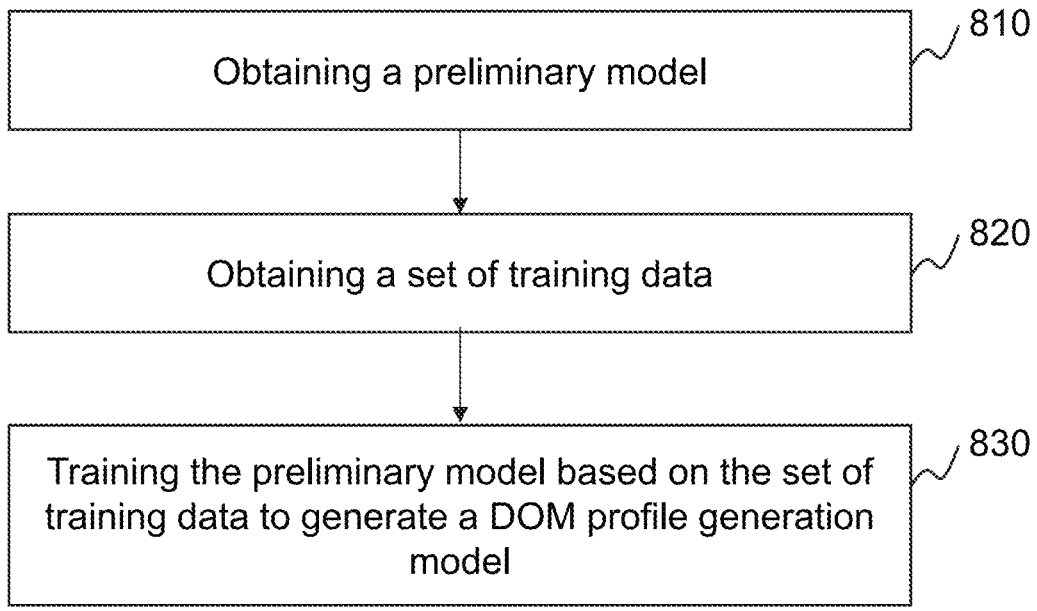
FIG. 8-A
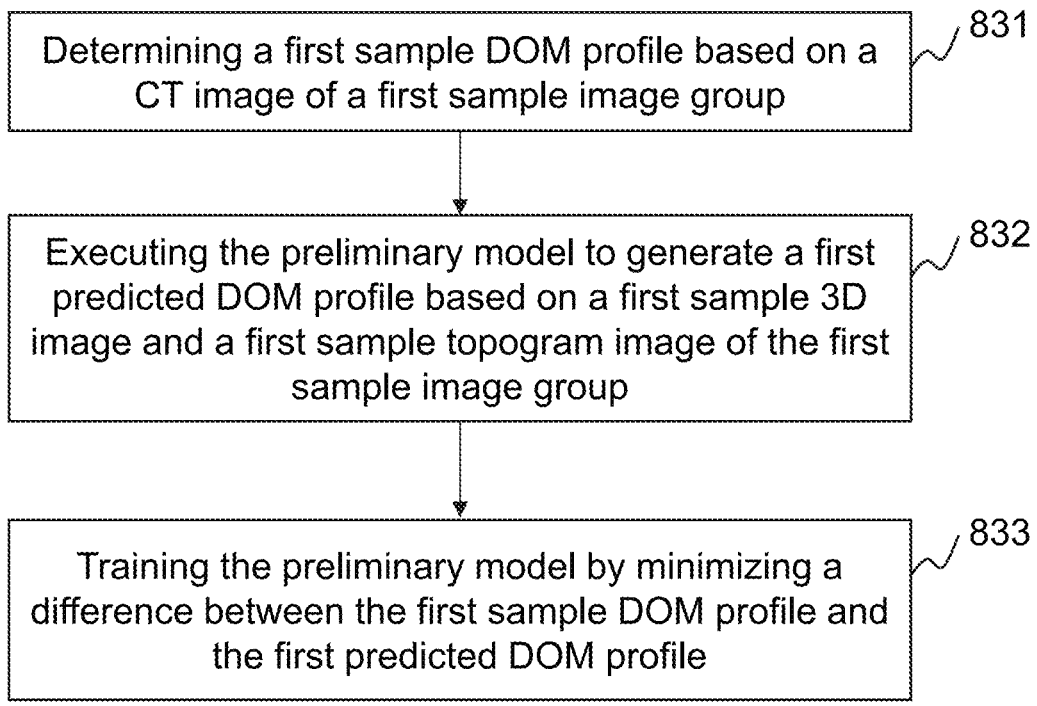
FIG. 8-B

METHODS AND SYSTEMS FOR MODULATING RADIATION DOSE

CROSS-REFERENCE TO RELATED APPLICATIONS

This application claims priority of Chinese Patent Application No. 201810715092.X, filed on Jun. 29, 2018, Chinese Patent Application No. 201810697936.2, filed on Jun. 29, 2018, and Chinese Patent Application No. 201810715382.4, filed on Jun. 29, 2018, the contents of each of which are hereby incorporated by reference.

TECHNICAL FIELD

This disclosure generally relates to methods and systems for modulating radiation dose during a computed tomography (CT) scan, and more particularly, to methods and systems for determining a dose of modulation (DOM) profile during a CT scan.

BACKGROUND

Tube current modulation (TCM) has become an effective method in reducing a CT radiation dose while maintaining a needed image quality during a CT scan. A topogram image may be used to determine a dose of modulation (DOM) profile and the DOM profile may be used as a reference in adjusting the tube current of a CT device. However, a conventional method for estimating the DOM profile may be inaccurate due to, e.g., the lack of information of the body shape of an object being scanned. Also, a conventional method usually generates a DOM profile as a whole without considering different properties in different regions (e.g., different organs or tissues) of the object.

SUMMARY

In an aspect of the present disclosure, a method is provided. The method may be implemented on a computing apparatus including a processor and a storage device for determining a dose of modulation (DOM) profile. The method may include obtaining a 3D image and a topogram image of the object. The method may further include obtaining a dose of modulation (DOM) profile generation model and executing the DOM profile generation model to generate a DOM profile related to a computed tomography (CT) scan of the object based on the 3D image and the topogram image of the object.

In some embodiments, the DOM profile generation model may be generated by a process including obtaining a preliminary model and a set of training data. The set of training data may include a plurality of sample CT images, a plurality of sample 3D images corresponding to the plurality of sample CT images, respectively, and a plurality of sample topogram images corresponding to the plurality of sample CT images, respectively. The process may also include training the preliminary model based on the set of training data to generate the DOM profile generation model.

In some embodiments, the training the preliminary model based on the set of training data to generate the DOM profile generation model may include determining a plurality of sample DOM profiles based on the plurality of sample CT images, executing the preliminary model based on the plurality of corresponding sample 3D images and the plurality of corresponding sample topogram images to generate a plurality of predicted DOM profiles, and training the preliminary model by minimizing differences between the plurality of predicted DOM profiles and the plurality of sample DOM profiles.

In some embodiments, the set of training data may be associated with multiple regions of the object and the generated DOM profile generation model is a universal model.

In some embodiments, the set of training data may be associated with a region of the object and the generated DOM profile generation model is a specialized model.

In some embodiments, the DOM profile generation model may include a neural network model.

In some embodiments, the 3D image of the object may be generated based on a stereoscopic vision technology, a structured light technology, or a Time-of-Flight (ToF) technology.

In some embodiments, the method may further include performing a localizer scan before the topogram of the object is obtained.

In some embodiments, the method may further include adjusting a tube current of a tube based on the generated DOM profile.

In another aspect of the present disclosure, a system is provided. The system may include an obtaining unit and a DOM profile generation unit. The obtaining unit may be configured to obtain a 3D image and a topogram image of an object. The obtaining unit may be further configured to obtain a DOM profile generation model. The DOM profile generation unit may execute the DOM profile generation model to generate a DOM profile related to a CT scan of the object based on the 3D image and the topogram image of the object.

In some embodiments, the system may further include a model training unit. The model training unit may be configured to obtaining a preliminary model and a set of training data. The set of training data may include a plurality of sample CT images, a plurality of sample 3D images corresponding to the plurality of sample CT images, respectively, and a plurality of sample topogram images corresponding to the plurality of sample CT images, respectively. The model training unit may be further configured to train the preliminary model based on the set of training data to generate the DOM profile generation model.

In some embodiments, to train the preliminary model based on the set of training data to generate the DOM profile generation model, the model training unit may be further configured to determining a plurality of sample DOM profiles based on the plurality of sample CT image, executing the preliminary model based on the plurality of corresponding sample 3D images and the plurality of corresponding sample topogram images to generate a plurality of predicted DOM profiles and training the preliminary model by minimizing differences between the plurality of predicted DOM profiles and the plurality of sample DOM profiles.

In another aspect of the present disclosure, a non-transitory computer readable medium storing instructions may be provided. The instructions, when executed by a computer, may cause the computer to implement a method. The method may include obtaining a 3D image and a topogram image of the object. The method may further include obtaining a dose of modulation (DOM) profile generation model and executing the DOM profile generation model to generate a DOM profile related to a computed tomography (CT) scan of the object based on the 3D image and the topogram image of the object.

In another aspect of the present disclosure, a method is provided. The method may include obtaining a 3D image of an object and determining a 3D contour of the object based on the 3D image. The method may further include, for each slice of a plurality of slices of the object, determining an X-ray dose corresponding to the each slice based on the 3D contour of the object. The method may further include generating a dose of modulation (DOM) profile based on the plurality of X-ray doses corresponding to the plurality of slices of the object.

In some embodiments, the 3D contour of the object may be a cylinder, an elliptic cylinder, or a cuboid.

In some embodiments, the object includes at least one of a head, a chest, a neck, an abdomen, a pelvis, or a leg of a patient.

In some embodiments, the determining 3D contour of the object based on the 3D image may include generating a preliminary 3D contour, determining a plurality of parameters of the preliminary 3D contour based on the 3D image of the object, and updating the preliminary 3D contour based on the plurality of parameters to generate the 3D contour of the object.

In some embodiments, the determining at least one X-ray dose corresponding to at least one slice of the object based on the 3D contour of the object may include generating at least one slice of the object based on the 3D contour of the object, determining a size of the at least one slice, obtaining a mapping table including a relationship between X-ray doses and sizes of slices, and searching the mapping table based on the size of the at least one slice to determine the at least one X-ray dose.

In another aspect of the present disclosure, a system is provided. The system may include an obtaining unit, a 3D contour determination unit and a DOM profile generation unit. The obtaining unit may be configured to obtain a 3D image of an object. The 3D contour determination unit may determine a 3D contour of the object based on the 3D image. The DOM profile generation unit may determine, for each slice of a plurality of slices of the object, an X-ray dose corresponding to the each slice based on the 3D contour of the object and generate a DOM profile based on the plurality of X-ray doses corresponding to the plurality of slices of the object.

In some embodiments, to determine a 3D contour of the object based on the 3D image, the 3D contour determination unit may be configured to generate a preliminary 3D contour, determine a plurality of parameters of the preliminary 3D contour based on the 3D image of the object, and update the preliminary 3D contour based on the plurality of parameters to generate the 3D contour of the object.

In some embodiments, to determine at least one X-ray dose corresponding to at least one slice of the object based on the 3D contour of the object, the DOM profile generation unit may be configured to generate at least one slice of the object based on the 3D contour of the object, determine a size of the at least one slice, obtain a mapping table including a relationship between X-ray doses and sizes of slices, and search the mapping table based on the size of the at least one X-ray dose.

In another aspect of the present disclosure, a non-transitory computer readable medium storing instructions may be provided. The instructions, when executed by a computer, may cause the computer to implement a method. The method may include obtaining a 3D image of an object and determining a 3D contour of the object based on the 3D image. The method may further include determining, for each slice of a plurality of slices of the object, an X-ray dose corresponding to the each slice of the object based on the 3D contour of the object. The method may further include generating a dose of modulation (DOM) profile based on the plurality of X-ray doses corresponding to the plurality of slices of the object.

In another aspect of the present disclosure, a method is provided. The method may include obtaining a topogram image of an object and segmenting the topogram image into a plurality of regions. The method may further include determining a plurality of regional dose of modulation (DOM) profiles. Each of the plurality of regional DOM profiles may correspond to one of the plurality of regions of the topogram image. The method may further include generating a DOM profile related to a computed tomography (CT) scan of the object based on the plurality of regional DOM profiles.

In some embodiments, the determining a plurality of regional DOM profiles may include extracting features of each of the plurality of regions, determining a reference topogram image for each of the plurality of regions based on the extracted features, and determining a regional DOM profile for each of the plurality of regions based on the corresponding reference topogram image.

In some embodiments, the determining a regional DOM profile for each of the plurality of regions based on the corresponding reference topogram image may include, for the each of the plurality of regions, obtaining a scan protocol associated with the corresponding reference topogram image and determining a regional DOM profile related to the each of the plurality of regions based on one or more parameters of the scan protocol associated with the corresponding reference topogram image.

In some embodiments, the determination of a regional DOM profile for each of the plurality of regions based on the corresponding reference topogram image may include: for the each of the plurality of regions, obtaining one or more image parameters associated with the region in the topogram image of the object, and determining a regional DOM profile related to the each of the plurality of regions based on one or more image parameters associated with the region in the topogram image and one or more parameters of the scan protocol associated with the corresponding reference topogram image.

In another aspect of the present disclosure, a system is provided. The system may include an obtaining unit, a segmentation unit, and a DOM profile generation unit. The obtaining unit may be configured to obtain a topogram image of an object. The segmentation unit may be configured to segment the topogram image into a plurality of regions. The DOM profile generation unit may be configured to determine a plurality of regional DOM profiles. Each of the plurality of regional DOM profiles corresponds to one of the plurality of regions of the topogram image. The DOM profile generation unit may be further configured to generate a DOM profile related to a CT scan of the object based on the plurality of regional DOM profiles.

In yet another aspect of the present disclosure, a non-transitory computer readable medium storing instructions may be provided. The instructions, when executed by a computer, may cause the computer to implement a method. The method may include obtaining a topogram image of an object and segmenting the topogram image into a plurality of regions. The method may further include determining a plurality of regional dose of modulation (DOM) profiles. Each of the plurality of regional DOM profiles may correspond to one of the plurality of regions of the topogram image. The method may further include generating a DOM profile related to a computed tomography (CT) scan of the object based on the plurality of regional DOM profiles.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 8-A and FIG. 8-B are flowcharts illustrating processes for training a DOM profile generation model according to some embodiments of the present disclosure;

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Figure 2:
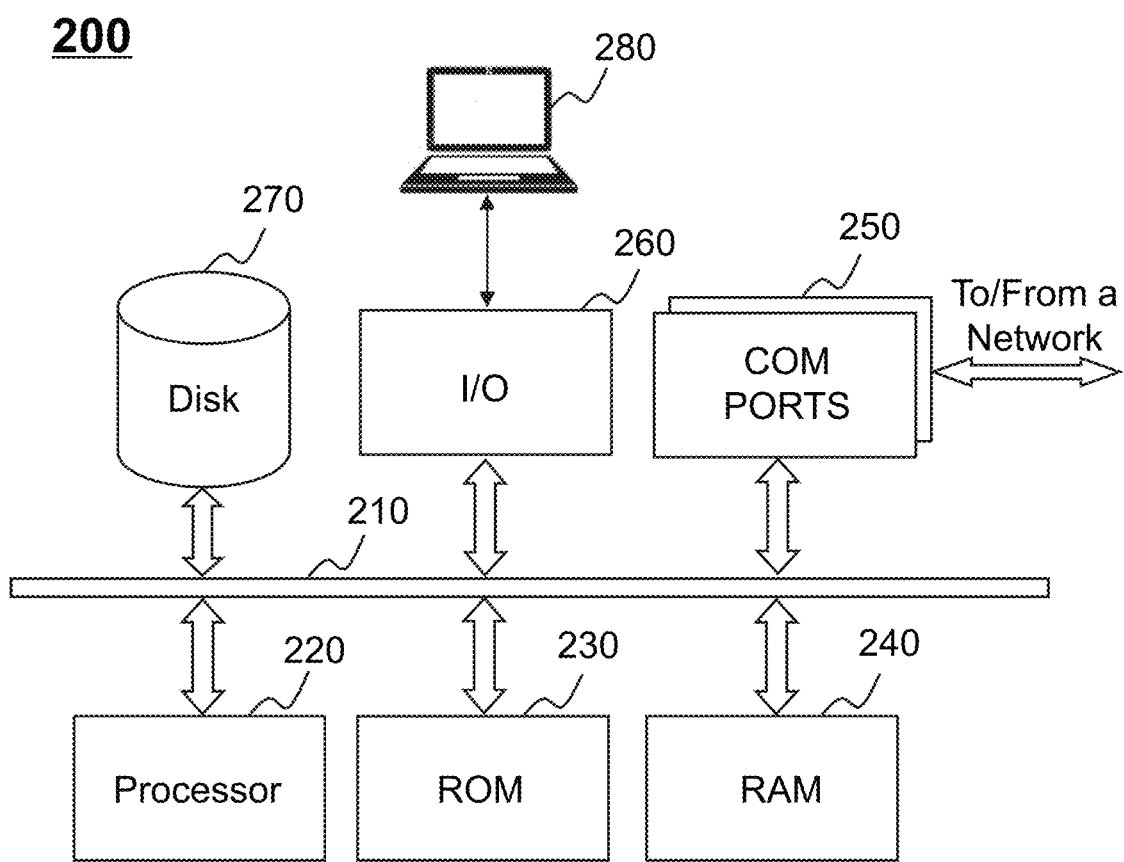
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 220 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The present disclosure relates to methods and systems for determining a dose of modulation (DOM) profile. In some embodiments, the method relates to determining the DOM profile based on an image of an object. In some embodiments, a topogram image may be used to estimate a shape (e.g., a 3D contour) of an object. For example, the shape of the object may be estimated based on attenuation data of the object in the topogram image. However, as the topogram image is a 2D image that corresponds to a fixed scan angle (usually vertically downwards), shape or size of the object, especially in the lateral and oblique directions, cannot be accurately estimated. In order to solve this problem, a 3D image may be used to generate a more accurate shape or 3D contour of the object. A radiation dose corresponding to each slice of the object (each corresponding to a particular scanning angle) may be determined based on the properties (e.g., thickness, width) of the 3D contour corresponding to the slice. A DOM profile may be determined according to the determined radiation doses.

In some embodiments, the method relates to determining the DOM profile based on a topogram image. For example, a topogram image of an object may be segmented into a plurality of regions. For each of the plurality of regions, a reference topogram image may be identified. A regional DOM profile may be determined for each reference topogram image and the regional DOM profiles may be combined to generate the DOM profile of the whole object.

In some embodiments, the method relates to determining the DOM profile based on both a topogram image and a 3D image of the object. For example, a DOM profile generation model may be obtained. The DOM profile generation model may be trained by a set of training data including a plurality of sample CT images, a plurality of sample topogram images, and a plurality of 3D images, of a plurality of objects. By executing a trained DOM profile generation model based on the topogram image and the 3D image of the object, a personalized DOM profile is generated.

Figure 1:
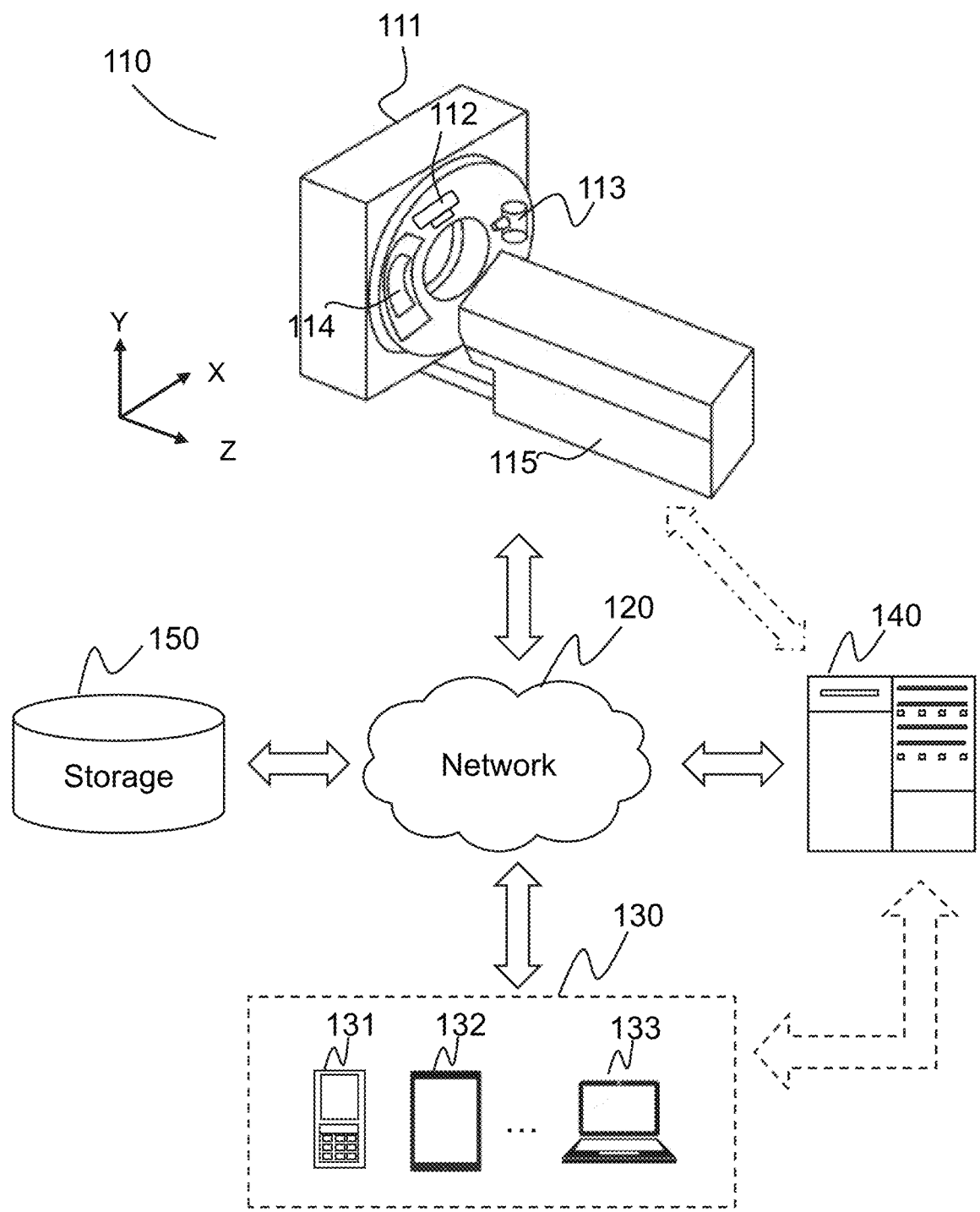
FIG. 1 is a schematic diagram illustrating an exemplary imaging system according to some embodiments of the present disclosure.

FIG. 1 is a schematic diagram illustrating an exemplary imaging system according to some embodiments of the present disclosure. In some embodiments, the imaging system 100 may scan an object and obtain corresponding scanning data. The imaging system 100 may generate an image based on the scanning data. The imaging system 100 may preprocess the scanning data or the generated image. The preprocessing of the scanning data or the generated image may include noise reduction, smoothing, correction, or the like, or any combination thereof.

In some embodiments, the imaging system 100 may be a medical imaging system. The medical imaging system may be a single modal imaging system or a multi modal imaging system. The single modal imaging system may include a PET (Positron Emission Tomography) device, a SPECT (Single Photon Emission Computed Tomography) device, a CT (Computed Tomography) device, an MRI (Magnetic Resonance Imaging) device, a DR (digital radiography) device, etc. The multimodal imaging system may include a PET-CT device, a PET-MRI device, a SPECT-MRI device, etc.

As shown in FIG. 1, the imaging system 100 may include a scanning device 110, a network 120, one or more terminals 130, a processing device 140, and storage 150.

The scanning device 110 may include a gantry 111, a 3D depth camera 112, a radioactive scanning source 113, a detector 114, and a table 115. A three-dimensional Cartesian coordinate system is illustrated in FIG. 1. The table 115 may hold an object (e.g., a patient). The Z-axis (also referred to as the Z-direction) may correspond to the long axis direction of the object. The X-Y plane (also referred to as a cross-sectional plane, or an axial plane) may correspond to a plane perpendicular to the Z-axis. The radioactive scanning source 113 and the detector 114 may rotate simultaneously and relatively to each other in the X-Y plane during a CT scan.

The gantry 111 may support the 3D depth camera 112, the radioactive scanning source 113, and the detector 114. In some embodiments, the table 115 may move along the Z-axis. The movement speed of the table 115 may be adjusted based on scanning time, scanning area, etc.

The 3D depth camera 112 may take a three-dimensional (3D) image (also referred to as a depth image) of an object. The 3D depth camera 112 may take 3D images from multiple angles including but not limited to from the front, from the top, from a side, etc. In some embodiments, the 3D depth camera may generate the 3D images based on a stereoscopic vision technology, a structured light technology, a Time-of-Flight (ToF) technology, or the like, or any combination thereof. In some embodiments, a 3D contour of the object may be estimated based on the 3D image.

The radioactive scanning source 113 may emit radioactive rays to the object. The radioactive rays may include microparticle rays, photon rays, etc. The microparticle rays may include neutrons, protons, electrons, p medium, heavy ions, or the like, or any combination thereof. The photon rays may include X-rays, y-rays, a-rays, p-rays, ultraviolet, lasers, or the like, or any combination thereof. In some embodiments, the radioactive scanning source 113 may rotate in the X-Y plane during a CT scan. In some embodiments, the radioactive scanning source 113 may be in a stationary position during a localizer scan.

The detector 114 may detect radioactive rays. At least some of the detected radioactive rays may have transmitted through the object. Readings (also referred to as scanning data) may be generated in response to the detected radioactive rays. In some embodiments, the detector 114 may include a scintillation detector (e.g., a cesium iodide detector), a gas detector, a circular detector, a square detector, an arcuate detector, or the like, or any combination thereof. In some embodiments, the detector may be a single-row detector or a multi-row detector.

The network 120 may include any suitable network that can facilitate exchange of information and/or data for the imaging system 100. In some embodiments, one or more components of the imaging system 100 (e.g., the scanning device 110, the terminal 130, the processing device 140, the database 150, etc.) may transmit or receive information and/or data with one or more other components of the imaging system 100 via the network 120. For example, the processing device 140 may obtain image data from the scanning device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanning device 110, the terminal 130, and/or the database 150. For example, the processing device 140 may process image data (e.g., a 3D image and/or a topogram image) and determine a dose of modulation (DOM) profile that may be used as a reference in adjusting tube current of the radioactive scanning source 113. In some embodiments, the processing device 140 may be a single server or a server group. The server group may be centralized or distributed. In some embodiments, the processing device 140 may be local or remote. For example, the processing device 140 may access information and/or data stored in the scanning device 110, the terminal 130, and/or the database 150 via the network 120. As another example, the processing device 140 may be directly connected to the scanning device 110, the terminal 130 and/or the database 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The database 150 may store data, instructions, and/or any other information. In some embodiments, the database 150 may store data obtained from the terminal 130 and/or the processing device 140. In some embodiments, the database 150 may store data and/or instructions that the processing device 140 may execute or use to perform exemplary methods described in the present disclosure. In some embodiments, the database 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the database 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the database 150 may be connected to the network 120 to communicate with one or more other components in the imaging system 100 (e.g., the processing device 140, the terminal 130, etc.). One or more components in the imaging system 100 may access the data or instructions stored in the database 150 via the network 120. In some embodiments, the database 150 may be directly connected to or communicate with one or more other components in the imaging system 100 (e.g., the processing device 140, the terminal 130, etc.). In some embodiments, the database 150 may be part of the processing device 140.

FIG. 2 is a schematic diagram illustrating an exemplary hardware and software components of a computing device according to some embodiments of the present disclosure.

The computing device 200 may be a general purpose computer or a special purpose computer, both may be used to implement an imaging system of the present disclosure. In some embodiments, the processing device 140 may be implemented on the computing device 200, via its hardware, software program, firmware, or a combination thereof. For example, the computing device 200 may obtain a three-dimensional (3D) image (also referred to as a depth image) and/or a topogram image and generate a dose of modulation (DOM) profile based on the 3D image and/or the topogram image. The computing device 200 may further adjust tube current of the radioactive scanning source 113 based on the DOM profile.

The computing device 200, for example, may include COM ports 250 connected to and from a network connected thereto to facilitate data communications. The computing device 200 may also include a (e.g., a central processing unit (CPU)) 220, in the form of one or more processors, for executing program instructions. The exemplary computer platform may include an internal communication bus 210, program storage and data storage of different forms, for example, a disk 270, and a read only memory (ROM) 230, or a random access memory (RAM) 240, for various data files to be processed and/or transmitted by the computer. The exemplary computer platform may also include program instructions stored in the ROM 230, RAM 240, and/or other type of non-transitory storage medium to be executed by the processor 220. The methods and/or processes of the present disclosure may be implemented as the program instructions. The computing device 200 also includes an I/O component 260, supporting input/output between the computer and other components therein such as user interface elements 280. The computing device 200 may also receive programming and data via network communications.

The computing device 200 may also include a hard disk controller communicated with a hard disk, a keypad/keyboard controller communicated with a keypad/keyboard, a serial interface controller communicated with a serial peripheral equipment, a parallel interface controller communicated with a parallel peripheral equipment, a display controller communicated with a display, or the like, or any combination thereof.

Merely for illustration, only one processor is described in the computing device 200. However, it should be note that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two different processors jointly or separately in the computing device 200 (e.g., the first processor executes operation A and the second processor executes operation B, or the first and second processors jointly execute operations A and B).

Figure 3:
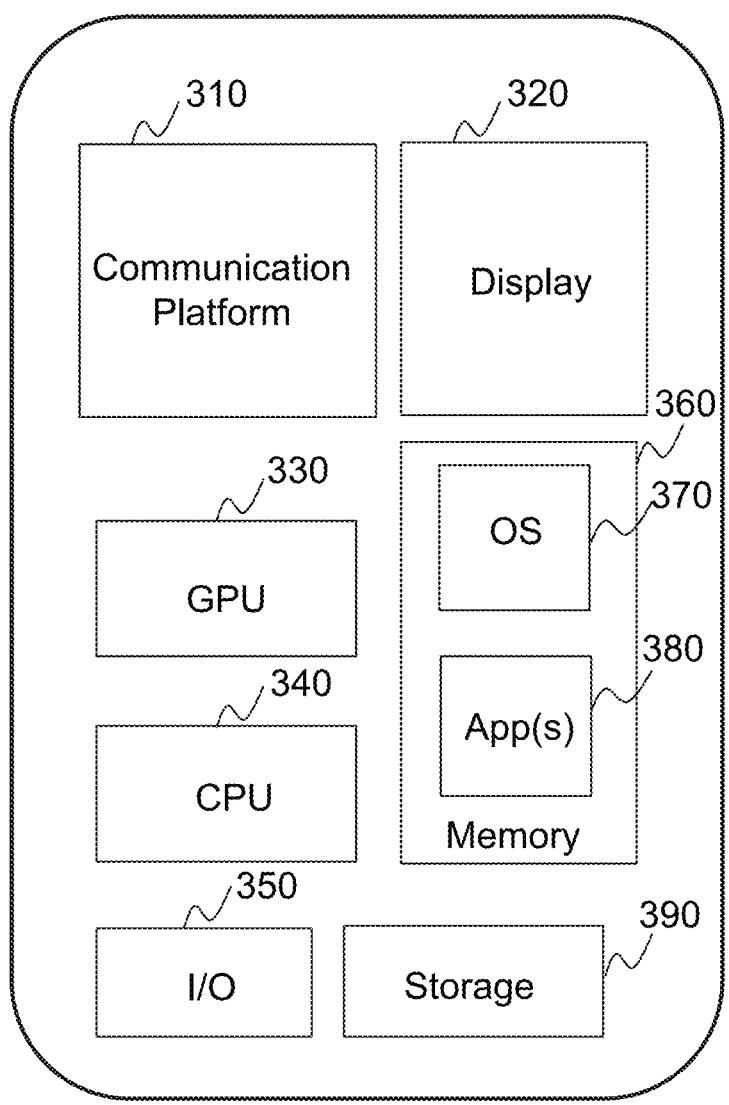
FIG. 3 is a schematic diagram illustrating exemplary hardware and/or software components of an exemplary mobile device that is configured to implement a specific system disclosed in the present disclosure.

FIG. 3 is a schematic diagram illustrating exemplary hardware and/or software components of a mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
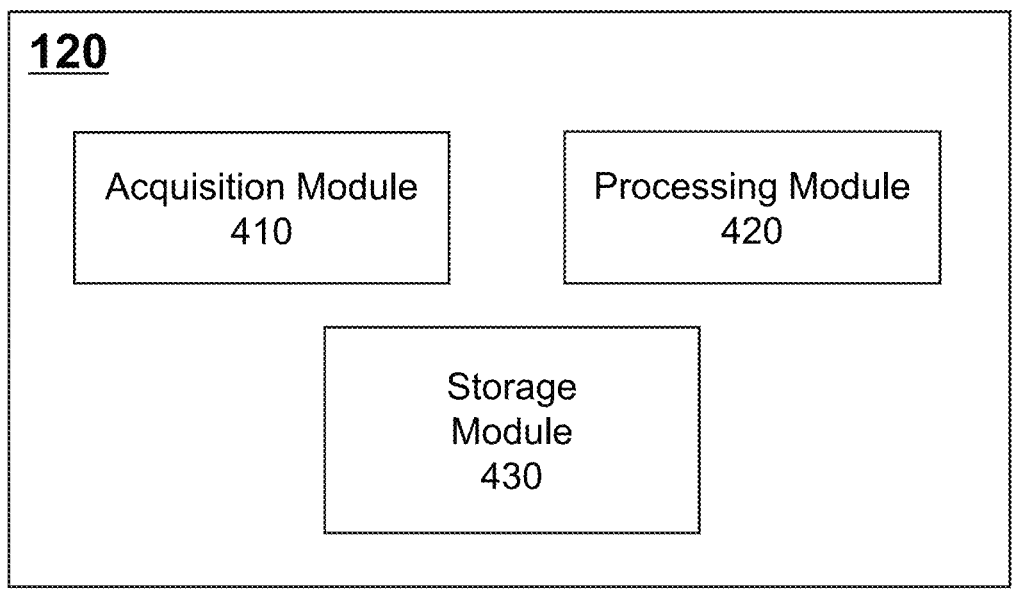
FIG. 4 is a schematic block diagram illustrating an exemplary processing device according to some embodiments of the present disclosure.

FIG. 4 is a schematic block diagram illustrating an exemplary processing device according to some embodiments of the present disclosure. The processing device 140 may include an acquisition module 410, a processing module 420, and a storage module 430.

The acquisition module 410 may be configured to acquire a three-dimensional (3D) image (also referred to as a depth image) and/or a topogram image of an object. The object may be a patient, or a tissue or organ of a patient (e.g., the head, the neck, the chest, the abdomen, the pelvis, etc.).

In some embodiments, the acquisition module 410 may acquire the 3D image of the object from a storage device (e.g., the storage 150, the disk 270, the memory 360, the storage module 430, a storage device external to the imaging system 100 (or referred to as an external storage device)). In some embodiments, the acquisition module 410 may acquire the 3D image of the object from a 3D depth camera (e.g., the 3D depth camera 112). In some embodiments, the 3D depth camera may take the 3D image of the object from multiple angles including but not limited to from the front, from the top, from a side, etc. The 3D depth camera may generate the 3D image based on the stereoscopic vision technology, the structured light technology, the Time-of-Flight (ToF) technology, or the like, or any combination thereof. In some embodiments, the acquisition module 410 may transmit the 3D image to the processing module 420 for further processing.

In some embodiments, the acquisition module 410 may acquire the topogram image of the object from a storage device (e.g., the storage 150, the disk 270, the memory 360, the storage module 430, an external storage device). In some embodiments, the acquisition module 410 may acquire topogram image data from the detector 114 and transmit the topogram image data to the processing module 420. The processing module 420 may further process (e.g., reconstruct) the topogram image data to generate the topogram image. In some embodiments, the topogram image may be associated with a localizer scan. A localizer scan may be performed by the scanning device 110 when the radioactive scanning source 113 is in a stationary position and the table 115 moves along the Z-axis (as shown in FIG. 1). For example, if the radioactive scanning source 113 is positioned above the object, an anterior-posterior (AP) topogram image may be obtained in a localizer scan. As another example, if the radioactive scanning source 113 is positioned on a side of the object, a lateral topogram image may be obtained in a localizer scan. In some embodiments, the acquisition module 410 may acquire an AP topogram image, a lateral topogram image, or both. The acquisition module 410 may then transmit the topogram image(s) to the processing module for further processing.

The processing module 420 may be configured to generate a dose of modulation (DOM) profile based on a 3D image and/or a topogram image. In some embodiments, the processing module 420 may generate the DOM profile based on both the 3D image and the topogram image. See, e.g., FIG. 7 and the descriptions thereof. In some embodiments, the processing module 420 may generate a DOM profile based on the 3D image only. See, e.g., FIG. 11 and the descriptions thereof. In some embodiments, the processing module 420 may generate a DOM profile based on the topogram image only. See, e.g., FIG. 13 and the descriptions thereof.

In some embodiments, the DOM profile or a regional DOM profile may be a continuous curve indicating a continuous change of the radiation dose over time or angle. In some embodiments, the DOM profile or a regional DOM profile may include one or more discrete points each of which corresponds to a radiation dose at a specific time or angle. In some embodiments, the DOM profile or a regional DOM profile may include a combination of one or more sections of continuous curves, or a combination of one or more sections of continuous curves and one or more discrete points. A data point of the DOM profile or a regional DOM profile may provide a degree of modulation of a radiation dose (also referred to as a radiation dose modulation, a dose of modulation, or a tube current modulation) in performing a CT scan on the object. The radiation dose modulation may be implemented by adjusting the tube current of the radioactive scanning source 113 based on the DOM profile during a CT scan. For example, during a helical CT scan, the radioactive scanning source 113 may rotate in the X-Y plane when the table 115 moves along the Z-axis. The dose modulation may be implemented by adjusting the tube current of the radioactive scanning source 113 in the X-Y plane and along the Z-axis based on the DOM profile during the helical CT scan.

In some embodiments, the DOM profile may show a relationship between radiation doses and time during a scan. The radiation dose may be associated with parameters in the scanning device 110, such as, a tube current-time product, a tube current, a tube voltage, a pitch, an effective dose, an absorbed dose, or the like. As used herein, a tube current-time product may refer to the product of the X-ray tube current (e.g., in milliamperes) of the radioactive scanning source 113 and the CT scanner exposure time per rotation (e.g., in seconds). As used herein, a tube voltage may indicate the peak energy of the x-ray photons (e.g., in kilovolts) in a spectrum of x-ray energies. As used herein, a pitch may refer to the ratio of table translation (table feed in centimeters per 360° gantry rotation) to the total nominal collimated x-ray beam width in the z direction in helical CT. As used herein, an absorbed dose may refer to the radiation energy of radiation received by a specific region of an object in a CT scan. As used herein, an effective dose may refer to a long-term effect of the radiation energy of radiation received by an object in a CT scan. A time point may correspond to a particular scanning angle (e.g., a particular configuration or position of the radioactive scanning source 113 in the X-Y plane). A time point during the scan may also correspond to a particular slice of the object at the corresponding scanning angle.

In some embodiments, the object may be divided to a plurality of slices along the Z-axis. The slices may be parallel to each other. The thickness of each slice may vary depending on one or more of different scan parameters. The thickness of the slices may be set by an operator (e.g., a nurse, a radiologist) or the imaging system 100. In some embodiments, the radioactive scanning source 113 may rotate 360° around the object to acquire CT image data corresponding to each slice of the object. When the table 115 moves along the Z-axis and the radioactive scanning source 113 rotates around the object, CT image data of a plurality of slices may be acquired.

The storage module 430 may be configured to store 3D images, topogram images, DOM profiles, or the like, or any combination thereof. In some embodiments, the storage 430 may store one or more programs and/or instructions that may be executed by the processor(s) of the processing device 140 to perform methods described in this disclosure. For example, the storage 430 may store program(s) and/or instruction(s) that may be executed by the processor(s) of the processing device 140 to obtain a 3D image and/or a topogram image of an object, generate a DOM profile based on the 3D image and/or the topogram image, and/or adjust the tube current of the radioactive scanning source 113 based on the DOM profile when a CT scan is performed on the object.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, the acquisition module 410 and processing module 420 may each include an independent storage unit.

Figure 5:
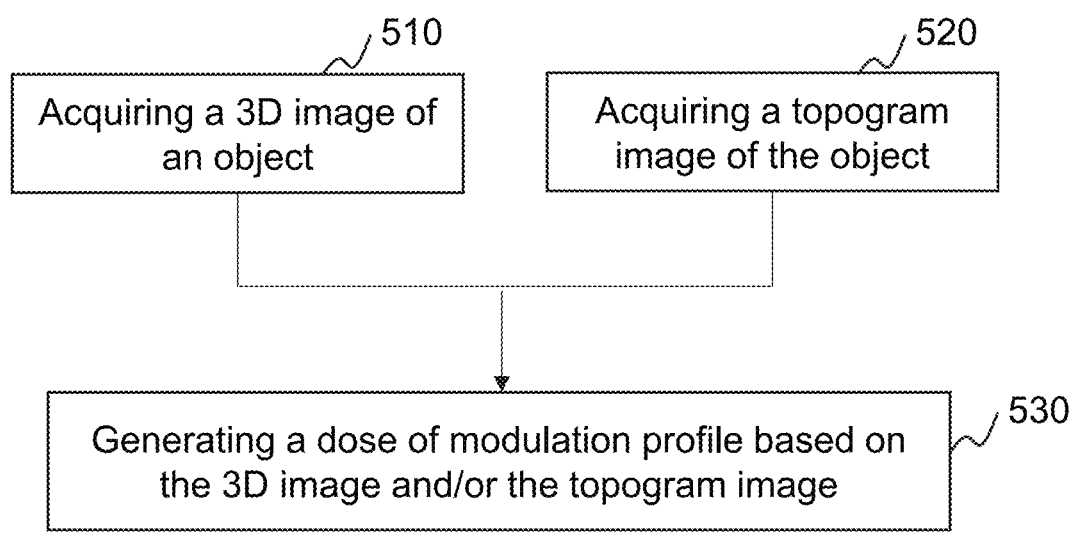
FIG. 5 is a flowchart illustrating an exemplary process for determining a dose of modulation (DOM) profile according to some embodiments of the present disclosure.

FIG. 5 is a flowchart illustrating an exemplary process for determining a dose of modulation (DOM) profile according to some embodiments of the present disclosure.

In 510, the acquisition module 410 may acquire a 3D image (also referred to as a depth image) of an object. The object may be a patient, or a tissue or organ of a patient (e.g., the head, the neck, the chest, the abdomen, the pelvis, etc.). The acquisition module 410 may acquire the 3D image of the object from a 3D depth camera (e.g., the 3D depth camera 112) or a storage device (e.g., the storage 150, the disk 270, the memory 360, the storage module 430, an external storage device). In some embodiments, the 3D depth camera may take the 3D image of the object from multiple angles including but not limited to from the front, from the top, from a side, etc. The 3D depth camera may generate the 3D image based on the stereoscopic vision technology, the structured light technology, the Time-of-Flight (ToF) technology, or the like, or any combination thereof.

In some embodiments, the 3D image may include pixels. A pixel in the 3D image may contain information relating to a corresponding point on the object. For instance, a pixel in the 3D image may contain information relating to the distance from the 3D depth camera to a corresponding point on the object, the greyscale value or color of the corresponding point on the object, or the like, or a combination thereof. The distance information of pixels in the 3D image may be used to provide a 3D contour of the object. In some embodiments, the 3D contour may include a cylinder, an elliptic cylinder, a cuboid, or the like. The 3D contour may include information of the surface structure or shape of the object, such as width, thickness, or the like, or any combination thereof.

In some embodiments, the 3D contour of the object may relate to radiation dose modulation in performing a CT scan on the object. For example, for two patients with different 3D contours, to get two CT images of substantially the same quality for diagnostic purposes, the patient with a larger 3D contour may need a higher radiation dose (or a higher tube current) during a CT scan than the patient with a smaller 3D contour.

In some embodiments, before a CT scan is performed on the object, radiation doses corresponding to different time points (or scanning angles) during a scan may be determined. The radiation doses corresponding to different time points during a scan may be determined and modulated based on the 3D image described herein.

In 520, the acquisition module 410 may acquire a topogram image of the object. The acquisition module 410 may acquire the topogram image of the object from a storage device (e.g., the storage 150, the disk 270, the memory 360, the storage module 430, an external storage device). The topogram image may be an AP topogram image or a lateral topogram image. In some embodiments, the acquisition module 410 may acquire both an AP topogram image and a lateral topogram image of the object in operation 520.

In some embodiments, the topogram image may include attenuation data of the object. The attenuation data in the topogram image may be used to estimate attenuation characteristics of the object. The attenuation characteristics of the object may relate to radiation dose modulation in performing a CT scan on the object. For example, a hard tissue (e.g., a bone), shown as a brighter region in a topogram image, may have a higher attenuation coefficient and need a higher radiation dose (corresponding to a higher tube current) during a CT scan than a soft tissue (e.g., lungs), shown as a darker region in the topogram image.

In some embodiments, the topogram image may correspond to a scan protocol. The scan protocol may relate to an anatomical region of the object, such as the head, the neck, the chest, or the like. For example, the scan protocol may include a head scan protocol, a neck scan protocol, a chest scan protocol, or the like. In some embodiments, the scan protocol may include scan parameters such as the voltage of the radioactive scanning source 113, a tube current-time product, a beam width, gantry rotation time, reconstruction kernel, or the like, or any combination thereof. In some embodiments, the scan protocol of a scan may include radiation doses and whether a DOM profile is used to modulate the radiation doses in the scan. Different scan protocols may have the same or different scan parameters. In some embodiments, the processing module 420 may determine the radiation dose of a CT scan based on the attenuation characteristics reflected in the topogram image and the specific scan protocol corresponding to the topogram.

In some embodiments, the topogram image may be used to estimate a shape of the object. For example, an AP topogram image may be used to estimate the width (also referred to as the X-coordinate value) of each slice of the object. As another example, a lateral topogram image may be used to estimate the thickness (also referred to as the Y-coordinate value) of each slice of the object.

In some embodiments, before a CT scan is performed on the object, radiation doses corresponding to different time points during a scan (or scanning angles) may be determined. The radiation doses corresponding to different time points during a scan may be determined and modulated based on the topogram image described herein.

In 530, the processing module 420 may generate a DOM profile based on the 3D image and/or the topogram image. In some embodiments, the processing module 420 may generate a DOM profile based on both the 3D image and the topogram image (see, e.g., FIG. 7 and the descriptions thereof). In some embodiments, the processing module 420 may generate a DOM profile based on the 3D image only (see, e.g., FIG. 11 and the descriptions thereof). In some embodiments, the processing module 420 may generate a DOM profile based on the topogram image only (see, e.g., FIG. 13 and the descriptions thereof).

The DOM profile may be a curve that provides a degree of modulation of a radiation dose (also referred to as a radiation dose modulation, a dose of modulation, or a tube current modulation) in performing a CT scan on the object. The radiation dose modulation may be implemented by adjusting the tube current of the radioactive scanning source 113 based on the DOM profile during a CT scan. For example, during a helical CT scan, the radioactive scanning source 113 may rotate in the X-Y plane when the table 115 moves along the Z-axis. The dose modulation may be implemented by adjusting tube current of the radioactive scanning source 113 in the X-Y plane and along the Z-axis based on the DOM profile during the helical CT scan.

In some embodiments, the DOM profile may show a relationship between radiation doses and time during a scan. The radiation dose may be associated with parameters in the scanning device 110, such as, a tube current-time product, a tube current, a tube voltage, a pitch, an effective dose, an absorbed dose, or the like. A scanning time or time point may correspond to a particular scanning angle (e.g., a particular configuration or position of the radioactive scanning source 113 in the X-Y plane). A time point during the scan may also correspond to a particular slice of the object at the corresponding scanning angle.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 510 may be performed after operation 520, or operation 510 and operation 520 may be performed simultaneously. As another example, operation 510 or operation 520 may be omitted in process 500. As a further example, the process 500 may include operations for generating the 3D image and/or the topogram image based on image data relating to the 3D image and/or the topogram image.

Figure 6:
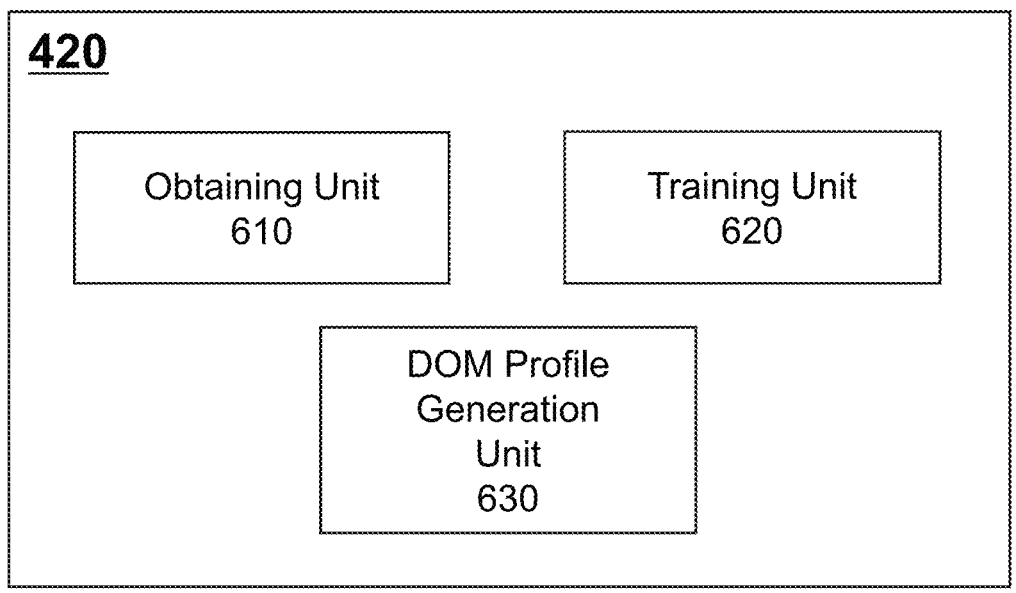
FIG. 6 is a schematic block diagram illustrating an exemplary processing module according to some embodiments of the present disclosure.

FIG. 6 is a schematic block diagram illustrating an exemplary processing module according to some embodiments of the present disclosure. The processing module 420 may include an obtaining unit 610, a training unit 620, and a DOM profile generation unit 630.

The obtaining unit 610 may be configured to obtain a three-dimensional (3D) image (also referred to as a depth image) and a topogram image of an object. The obtaining unit 610 may obtain the 3D image and the topogram image of the object from a storage device (e.g., the storage 150, the disk 270, the memory 360, the storage module 430, an external storage device).

In some embodiments, the 3D image may include pixels. A pixel in the 3D image may contain information relating to a corresponding point on the object. For instance, a pixel in the 3D image may contain information relating to the distance from the 3D depth camera to a corresponding point on the object, the greyscale value or color of the corresponding point on the object, or the like, or a combination thereof. The distance information of pixels in the 3D image may be used to provide a 3D contour of the object. In some embodiments, the 3D contour may include a cylinder, an elliptic cylinder, a cuboid, or the like. The 3D contour may include information of the surface structure or shape of the object, such as width, thickness, or the like, or any combination thereof.

In some embodiments, the 3D contour of the object may relate to radiation dose modulation in performing a CT scan on the object. For example, for two patients with different 3D contours, to get two CT images of substantially the same quality for diagnostic purposes, the patient with a bigger 3D contour may need a higher radiation dose (or a higher tube current) during a CT scan than the patient with a smaller 3D contour.

In some embodiments, the topogram image may include attenuation data of the object. The attenuation data in the topogram image may be used to estimate attenuation characteristics of the object. The attenuation characteristics of the object may relate to radiation dose modulation in performing a CT scan on the object. For example, a hard tissue (e.g., a bone), identified as a brighter region in a topogram image, may have a higher attenuation coefficient and need a higher radiation dose (corresponding to a higher tube current) during a CT scan than a soft tissue (e.g., lungs), identified as a darker region in the topogram image.

In some embodiments, before a CT scan is performed on the object, radiation doses corresponding to different time points (or scanning angles) during a scan may be determined. The radiation doses corresponding to different time points during a scan may be determined and modulated based on the 3D image and the topogram image described herein.

The training unit 620 may be configured to train a DOM profile generation model. The training unit 620 may train the DOM profile generation model based on a set of training data. The set of training data may include a plurality of sample CT images, a plurality of sample 3D images, and a plurality of sample topogram images. The DOM profile generation model may be an Artificial Neural Network (ANN) model such as a Convolutional Neural Network (CNN) model, a Recurrent Neural Network (RNN) model, etc. In some embodiments, the DOM profile generation model may be transmitted to a storage device (e.g., the storage 150, the disk 270, the memory 360, the storage module 430, an external storage device) to be stored. In some embodiments, the DOM profile generation model may be a universal model or a specialized model. A universal model may be used to generate a DOM profile corresponding to one or more of multiple types of 3D images and topogram images of multiple objects or multiple regions of an object. The universal model may be trained based on a plurality of sample 3D images, a plurality of sample CT images, and a plurality of sample topogram images that are associated with one or more of different regions of a type of object (e.g., a human body). The plurality of sample 3D images, the plurality of sample CT images, and the plurality of sample topograms may be obtained from same or different regions of same or different objects. The different objects may have same or different ages, body shapes, etc. For example, the objects may include infants, children, adults, elders, males, females, overweight people, underweight people, etc. In some embodiments, the plurality of sample 3D images, the plurality of sample CT images, and the plurality of sample topogram images that are used in training may collectively cover a whole human body or a whole upper body. For example, the universal model may be a whole body model that may generate a DOM profile of any region (e.g., a head, a chest, a neck, an abdomen, a pelvis, or a leg) of an object based on a 3D image and a topogram image of the object regardless of the age, the size, or the body shapes of the object. A specialized model may correspond to a specific object or body region. For example, a specialized model of a brain may be used for generating a DOM profile (or referred to as a regional DOM profile elsewhere in the present application) of a brain based on a 3D image and a topogram image. The specialized model of a brain may be trained by a set of training data corresponding to brains. As another example, an infant-brain specialized model may be used specifically for generating a DOM profile of a brain region of an infant based on a 3D image and a topogram image of the infant. The infant-brain specialized model may be trained by a set of training data corresponding to brains of infants.

The DOM profile generation unit 630 may be configured to generate a DOM profile. The DOM profile generation unit 630 may generate the DOM profile based on the 3D image and the topogram image obtained by the obtaining unit 610 and the DOM profile generation model trained by the training unit 620.

It should be noted that the above description is merely provided for the purposes of illustration, and not intended to limit the s cope of the present disclosure. For persons having ordinary skills in the art, multiple variations or modifications may be made under the teachings of the present disclosure. However, those variations and modifications do not depart from the scope of the present disclosure. For instance, the training unit 620 may be omitted. The DOM profile generation unit 630 may retrieve a DOM profile generation model from a library. The library may include a plurality of universal and/or specialized DOM profile generation models. The library may be stored in a storage device (e.g., the storage 150, the disk 270, the memory 360, the storage module 430, an external storage devices) that is accessible by the data processing device 140 or a portion thereof via, e.g., the internet 120.

Figure 7:
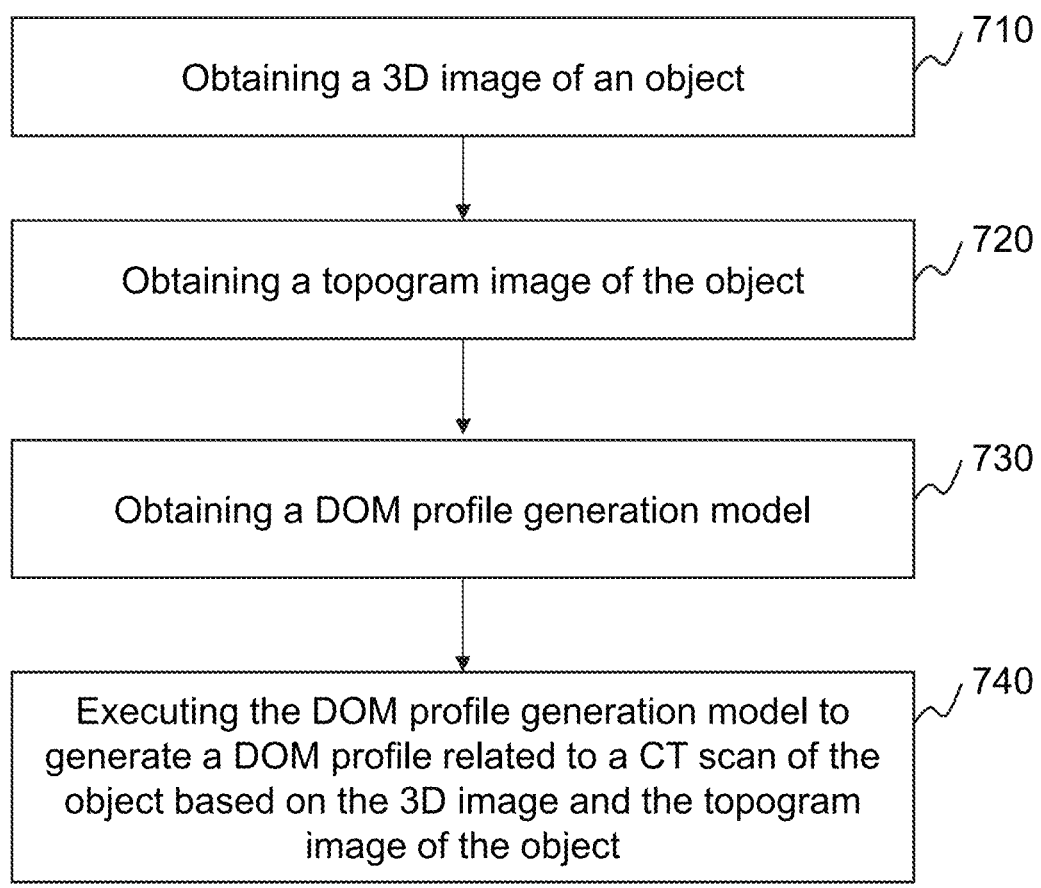
FIG. 7 is a flowchart illustrating an exemplary process for determining a DOM profile based on a 3D image and a topogram image according to some embodiments of the present disclosure.

FIG. 7 is a flowchart illustrating an exemplary process for determining a DOM profile based on a 3D image and a topogram image according to some embodiments of the present disclosure.

In 710, the obtaining unit 610 may obtain a 3D image of an object. The obtaining unit 610 may obtain the 3D image of the object from a storage device (e.g., the storage 150, the disk 270, the memory 360, the storage module 430, an external storage device). In some embodiments, the obtaining unit 610 may obtain the 3D image of the object by a 3D depth camera (e.g., the 3D depth camera 112). In some embodiments, the 3D depth camera may take the 3D image of the object from multiple angles including but not limited to from the front, from the bottom, from a side, etc. The 3D depth camera may generate the 3D image based on a stereoscopic vision technology, a structured light technology, a Time-of-Flight (ToF) technology, or the like, or any combination thereof.

In some embodiments, the 3D image may include pixels. A pixel in the 3D image may contain information relating to a corresponding point on the object. For instance, a pixel in the 3D image may contain information relating to the distance from the 3D depth camera to a corresponding point on the object, the greyscale value or color of the corresponding point on the object, or the like, or a combination thereof. The distance information of pixels in the 3D image may be used to provide a 3D contour of the object. In some embodiments, the 3D contour may include a cylinder, an elliptic cylinder, a cuboid, or the like. The 3D contour may include information of the surface structure or shape of the object, such as width, thickness, or the like, or any combination thereof.

In some embodiments, the 3D contour of the object may relate to radiation dose modulation in performing a CT scan on the object. For example, for two patients with different 3D contours, to get two CT images of substantially the same quality for diagnostic purposes, the patient with a bigger 3D contour may need a higher radiation dose (or a higher tube current) during a CT scan than the patient with a smaller 3D contour.

In 720, the obtaining unit 610 may obtain a topogram image of the object. The obtaining unit 610 may obtain the topogram image of the object from a storage device (e.g., the storage 150, the disk 270, the memory 360, the storage module 430, an external storage device). The topogram image may be an AP topogram image or a lateral topogram image. In some embodiments, the obtaining unit 610 may obtain both an AP topogram image and a lateral topogram image of the object in operation 720.

In some embodiments, the topogram image may include attenuation data of the object. The attenuation data in the topogram image may be used to estimate attenuation characteristics of the object. The attenuation characteristics of the object may relate to radiation dose modulation in performing a CT scan on the object. For example, a hard tissue (e.g., a bone), identified as a brighter region in a topogram image, may have a higher attenuation coefficient and need a higher radiation dose (corresponding to a higher tube current) during a CT scan than a soft tissue (e.g., lungs), identified as a darker region in the topogram image.

In some embodiments, the 3D image obtained in operation 710 and the topogram image obtained in operation 720 may be based on data acquired in one or more scans from a same angle or different angles. It should be noted that the topogram image may be used to estimate both the attenuation characteristics and the shape of the object. In some embodiments, the shape of the object may be estimated based on the 3D image instead of the topogram image.

In 730, the DOM profile generation unit 630 may obtain a DOM profile generation model. The DOM profile generation unit 630 may obtain the DOM profile generation model from a storage device (e.g., the storage 150, the disk 270, the memory 360, the storage module 430, an external storage device). The DOM profile generation model may be pre-trained by the model training unit 620. The detailed description regarding the generation of the DOM profile generation model may be found elsewhere in the present disclosure (e.g., FIG. 8 and the descriptions thereof).

In 740, DOM profile generation unit 630 may execute the DOM profile generation model to generate a DOM profile related to a CT scan of the object based on the 3D image and the topogram image of the object. More particularly, the 3D image and the topogram image of the object may be inputted to the pre-trained DOM profile generation model by the DOM profile generation unit 630 and in response to the inputted 3D image and the topogram image, the DOM profile generation model may generate a DOM profile as an output.

The DOM profile may be a curve that provides a degree of modulation of a radiation dose (also referred to as a radiation dose modulation, a dose of modulation, or a tube current modulation) in performing a CT scan on the object. The radiation dose modulation may be implemented by adjusting tube current of the radioactive scanning source 113 based on the DOM profile during a CT scan. For example, during a helical CT scan, the radioactive scanning source 113 may rotate in the X-Y plane when the table 115 moves along the Z-axis. The dose modulation may be implemented by adjusting tube current of the radioactive scanning source 113 in the X-Y plane and along the Z-axis based on the DOM profile during the helical CT scan.

In some embodiments, the DOM profile may show a relationship between radiation doses and time during a scan. The radiation dose may be associated with parameters in the scanning device 110, such as, a tube current-time product, a tube current, a tube voltage, a pitch, an effective dose, an absorbed dose, or the like. A scanning time may correspond to a particular scanning angle (e.g., a particular configuration or position of the radioactive scanning source 113 in the X-Y plane). A time point during the scan may also correspond to a particular slice of the object at the corresponding scanning angle. In some embodiments, the DOM profile may be a continuous curve indicating a continuous change of the radiation dose over time or angle. In some embodiments, the DOM profile may include one or more discrete points each of which corresponds to a radiation dose at a specific time or angle. In some embodiments, the DOM profile may include a combination of one or more sections of continuous curves, or a combination of one or more sections of continuous curves and one or more discrete points.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 710 may be performed after operation 720, or operation 710 and operation 720 may be performed simultaneously. As another example, the process 700 may include operations for generating the 3D image and/or the topogram image based on image data relating to the 3D image and/or the topogram image.

FIG. 8-A and FIG. 8-B are flowcharts illustrating exemplary processes for training a DOM profile generation model according to some embodiments of the present disclosure.

In 810, the training unit 620 may obtain a preliminary model. The preliminary model may be an Artificial Neural Network (ANN) model such as a Convolutional Neural Network (CNN) model, a Recurrent Neural Network (RNN) model, etc. The preliminary model may include a plurality of preliminary parameters. In some embodiments, the preliminary model may be predefined. For example, the inner structure or the preliminary parameters of the preliminary model may be predefined according to one or more characteristics (e.g., size, thickness, complexity) of a specific object (e.g., the chest, the head) that the preliminary model is associated with.

In 820, the training unit 620 may obtain a set of training data. In some embodiments, the training unit 620 may obtain the set of training data from a storage device (e.g., the storage 150, the disk 270, the memory 360, the storage module 430, an external storage device). The set of training data may include a plurality of sample CT images, a plurality of sample 3D images, and a plurality of sample topogram images. A sample CT image of the plurality of sample CT images may correspond to one of the plurality of sample 3D images and one of the plurality of sample topogram images. As used herein, the correspondence between a CT image, a 3D image, and a topogram image indicates that the images represent a same area or region of an object. For brevity, a sample CT image and its corresponding sample 3D image and sample topogram image may be designated as a sample image group. Accordingly, the set of training data may include a plurality of sample image groups. In some embodiments, a sample image group may be associated with a same object or a same region of an object. In some embodiments, the plurality of sample image groups may be associated with a same or different objects or a same or different regions of one or more objects.

In 830, the training unit 620 may train the preliminary model based on the set of training data to generate the DOM profile generation model. For example, in the case that the plurality of sample image groups in the set of training data are associated with a same region of one or more objects (e.g. brain, head, chest, leg), a specialized DOM profile generation model may be generated. As another example, in the case that the plurality of sample image groups are associated with different regions of an object, a generalized DOM profile generation model may be generated. The training unit 620 may generate the DOM profile generation model by updating the plurality of preliminary parameters. In some embodiments, operation 830 may be further split into operations 831-833 as illustrated in FIG. 8B.

In 831, for a first sample image group of the set of training data, the training unit 620 may determine a first sample DOM profile based on a first sample CT image of the first sample image group. The first sample CT image may include attenuation data. In some embodiments, the training unit 620 may generate the first sample DOM profile corresponding to the first sample CT image based on the attenuation data included in the first sample CT image. In some embodiments, the training unit 620 may search for and retrieve the first sample DOM profile corresponding to the first sample CT image of the first sample image group from a storage device (e.g., the storage 150, the disk 270, the memory 360, the storage module 430, an external storage device).

In 832, the training unit 620 may execute the preliminary model to generate a first predicted DOM profile based on a first sample 3D image and a first sample topogram image of the first sample image group.

In 833, the training unit 620 may train the preliminary model by minimizing difference between the first sample DOM profile and its corresponding first predicted DOM profile. Correspondingly, the training unit 620 may update at least one of the plurality of preliminary parameters of the preliminary model and generate a first updated model based on the plurality of updated preliminary parameters.

Operations 831-833 may be performed repeatedly. In some embodiments, the difference between the sample DOM profile (e.g., the first DOM profile and the succeeding ones) and the corresponding predicted DOM profile may be assessed in terms of a loss function. The loss function may include but not limited to an L1 norm loss function, an L2 norm loss function, a quadratic cost function, a cross-entropy loss function, a log-likelihood cost function, or the like, or any combination thereof. In some embodiments, the preliminary model may be updated by different strategies. For example, if the difference between the sample DOM profile and the predicted DOM profile in the present iteration is less than a threshold (e.g., the difference determined in the preceding iteration), part or all parameters of the preliminary model may be updated. If the difference between sample DOM profile and the predicted DOM profile in the present iteration is great than the difference in the preceding iteration, the preliminary model is not updated in the current round of iteration. In some embodiments, the training unit 620 may terminate the iterations of operations 831-833 and generate a trained DOM profile generation model until all of the plurality of the sample image groups in the training data are traversed or a preset condition is satisfied. An exemplary preset condition may include that the difference between a sample DOM profile and its corresponding predicted DOM profile is less than a threshold in one or more consecutive iterations.

Compared with a method of estimating the DOM profile solely based on merely a 3D image or a topogram image, the method(s) disclosed in process 800 may be beneficial (e.g., may generate a more accurate DOM profile). The sample CT image used to train the DOM profile generation model may contain CT image data that correspond to an exact DOM profile of the object. Training with the exact DOM profile of the object may generate an accurate DOM profile. The accuracy of the DOM profile generated by the DOM profile generation model may be further improved if the sample CT image is obtained at a higher quality (e.g., higher resolution). Moreover, the 3D image may generally generate a more accurate estimation on the shape, size and/or the 3D contour of the object than the topogram, while the topogram may generally contain attenuation data corresponding to the inner structure of the object which may facilitate the determination of the DOM profile. The method(s) disclosed in process 800 may use both the 3D image and the topogram of the object as an input to the DOM profile generation model to generate a more accurate DOM profile because of their respective advantages. It should be noted that even though using both the 3D image and the topogram image as an input of the DOM profile generation model may show slight advantage over solely topogram image or 3D image in certain scenarios, determining the DOM profile by inputting solely the topogram image or the 3D image into the DOM profile generation model is also within the protection scope of the present disclosure.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, operation 810 may be performed after operation 820, or operation 810 and operation 820 may be performed simultaneously.

Figure 9:
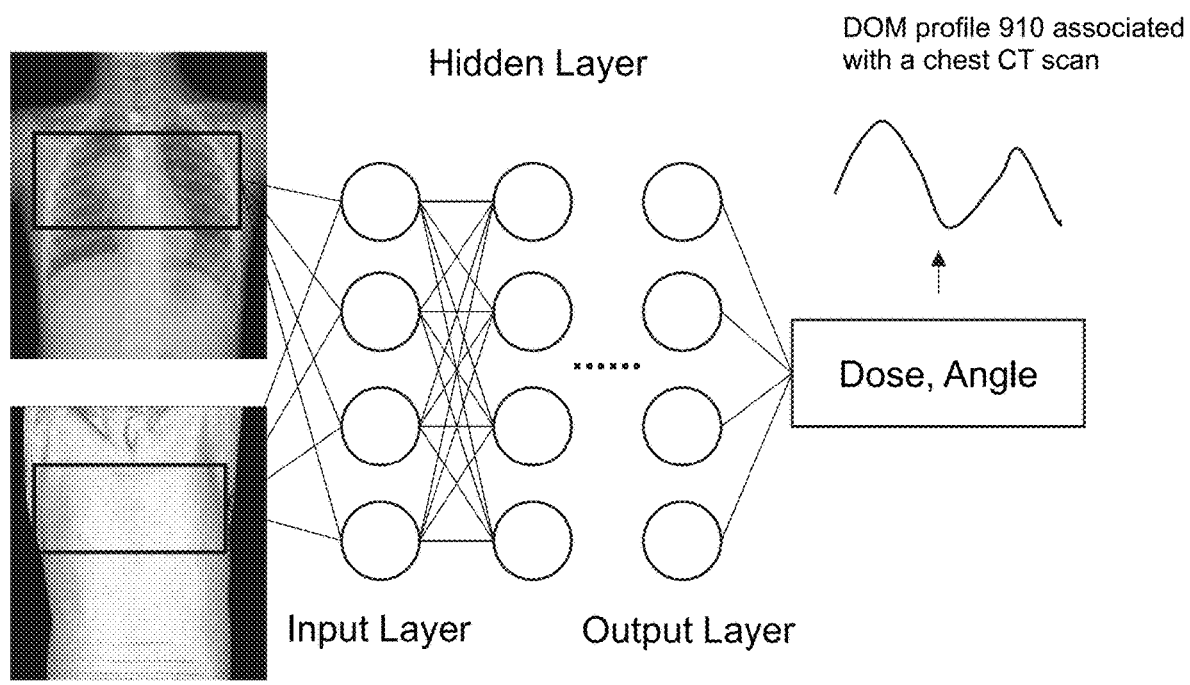
FIG. 9 is a schematic diagram illustrating an exemplary structure of a DOM profile generation model according to some embodiments of the present disclosure.

FIG. 9 is a schematic diagram illustrating an exemplary structure of a DOM profile generation model according to some embodiments of the present disclosure. As shown in FIG. 9, the DOM profile generation model may be a Convolutional Neural Network (CNN) model. The CNN model may include an input layer, a hidden layer, and an output layer, and each node in FIG. 9 may simulate a neuron. The hidden layer may include a plurality of convolutional layers, a plurality of pooling layers, and/or a plurality of fully connected layers (not shown in FIG. 9). After the CNN model is trained by, e.g., process 800 illustrated in FIG. 8, the CNN model may be configured to generate a DOM profile in response to its input. In some embodiments, the input of the CNN may include a topogram image (e.g., an AP topogram image or a lateral topogram image) and a 3D image of an object. In some embodiments, the input of the CNN may include two topogram images (e.g., an AP topogram image and a lateral topogram image) and a 3D image of an object.

In some embodiments, the DOM profile generated based on the DOM profile generation model may be associated with an anatomical region of an object on which a CT scan is performed. The anatomical region of the object may include the head, the neck, the chest, or the like, or any combination thereof. In some embodiments, the anatomical region of the object may be automatically determined based on a scan protocol set by the imaging system 100 or an operator (e.g., a nurse, a radiologist). In some embodiments, the anatomical region of the object may be marked manually by the operator (e.g., a nurse, a radiologist) in a 3D image and/or a topogram image of the object.

For example, an operator (e.g., a nurse, a radiologist) may perform a localizer scan on a patient to acquire an AP and/or a lateral topogram image of the patient, take a 3D image of the patient, and select a chest scan protocol. In some embodiments, the processing device 140 may automatically determine the chest of the patient as the anatomical region on which a CT is performed based on the selected scan protocol. In some embodiments, the operator may manually mark a region including the chest of the patient in the 3D image and/or the topogram image. In some embodiments, the anatomical region on which a CT scan is performed may be determined based on both the selected scan protocol and any manual adjustment or relevant input of the operator. The CNN model may further generate a DOM profile 910 associated with a chest CT scan (as shown in FIG. 9) based on the AP and/or lateral topogram image and the 3D image. In some embodiments, the CNN model may generate multiple doses and their corresponding angles in the output layer and may construct (e.g., by interpolation) a DOM profile 910 based on the multiple doses and angles.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the DOM profile generation model may be another type of model including but not limited to a support vector machine, a decision tree, other types of an ANN model, a deep learning model, a Bayesian network, or the like, or any combination thereof.

Figure 10:
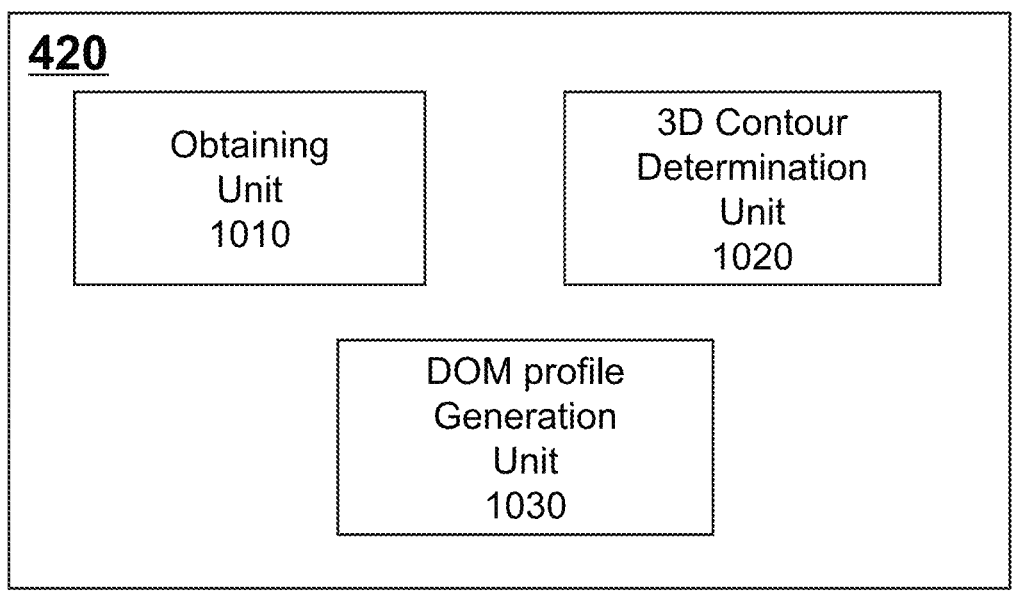
FIG. 10 is a schematic block diagram illustrating an exemplary processing module according to some embodiments of the present disclosure.

FIG. 10 is a schematic block diagram illustrating an exemplary processing module according to some embodiments of the present disclosure. The processing module 420 may include an obtaining unit 1010, a 3D contour determination unit 1020, and a DOM profile generation unit 1030.

The obtaining unit 1010 may be configured to obtain a three-dimensional (3D) image (also referred to as a depth image) of an object. In some embodiments, the obtaining unit 1010 may obtain the 3D image of the object from a storage device (e.g., the storage 150, the disk 270, the memory 360, the storage module 430, an external storage device). In some embodiments, the obtaining unit 1010 may obtain the 3D image of the object from an imaging device (e.g., a 3D depth camera).

In some embodiments, the 3D image may be taken by a 3D depth camera. A 3D contour of an object may be estimated based on the 3D image. The 3D depth camera may generate the 3D image based on a stereoscopic vision technology, a structured light technology, a Time-of-Flight (ToF) technology, or the like, or any combination thereof. In some embodiments, the 3D depth camera may take the 3D image of the object from multiple angles including but not limited to, from the front, from the top, from a side, etc.

The 3D contour determination unit 1020 may be configured to determine a 3D contour of an object based on a 3D image. The 3D image may include pixels. A pixel in the 3D image may contain information relating to a corresponding point on the object. For instance, a pixel in the 3D image may contain information relating to the distance from the 3D depth camera to a corresponding point on the object, the greyscale value or color of the corresponding point on the object, or the like, or a combination thereof. The distance information of pixels in the 3D image may be used to provide a 3D contour of the object. In some embodiments, the 3D contour may include a cylinder, an elliptic cylinder, a cuboid, or the like. The 3D contour may include information of the surface structure or shape of the object, such as width, thickness, or the like, or any combination thereof. In some embodiments, a preliminary 3D contour may be generated. The preliminary 3D contour may be a geometrical shape with a plurality of default parameters. The plurality of parameters of the preliminary 3D contour based on the 3D image of the object may be determined. The preliminary 3D contour may be updated based on the plurality of parameters to generate the 3D contour of the object.

The DOM profile generation unit 1030 may be configured to generate a DOM profile based on a 3D image of an object. For a slice of the object, the DOM profile generation unit 1030 may first determine a radiation dose. The radiation dose may be determined based on the 3D contour of the object (e.g., the shape, the thickness) and/or the organs or tissues within the slice of the object. The DOM profile generation unit 1030 may generate the DOM profile based on a plurality of radiation doses corresponding to a plurality of slices of the object. The DOM profile may be used as a reference in performing the radiation dose modulation by way of, e.g., adjusting the tube current of the radioactive scanning source 113 during a CT scan.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, one or more units in the processing module 420 may each include an independent storage unit.

Figure 11:
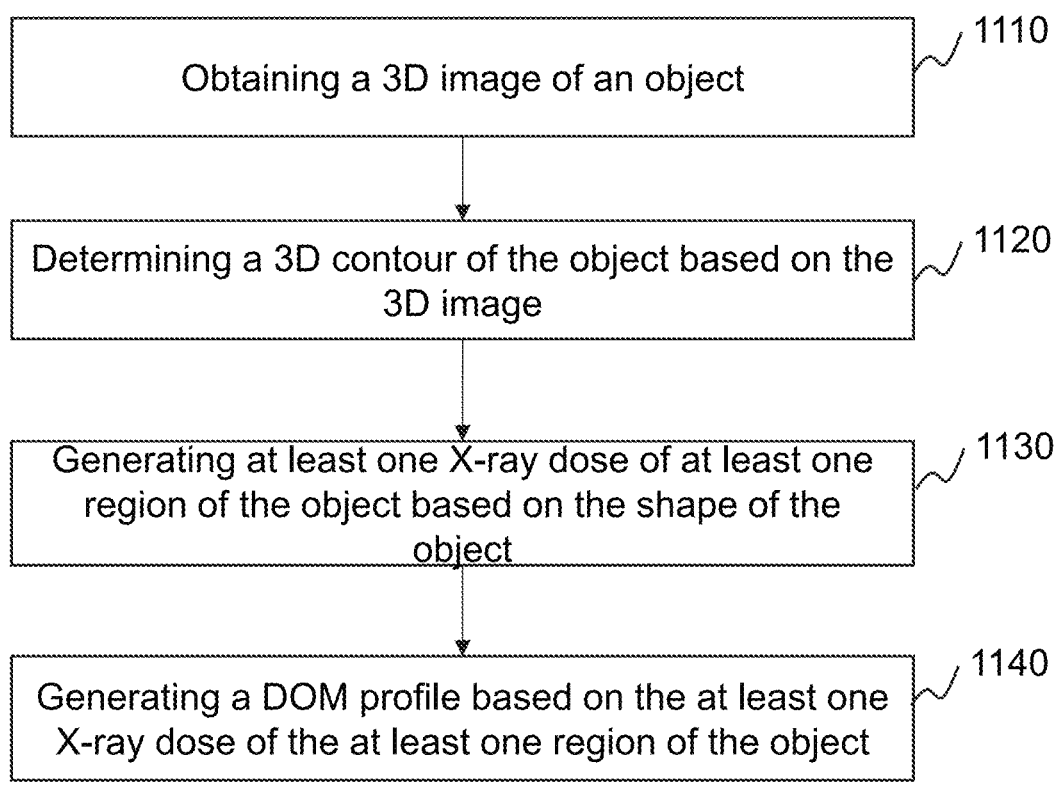
FIG. 11 is a flowchart illustrating an exemplary process for determining a DOM profile based on a 3D image according to some embodiments of the present disclosure.

FIG. 11 is a flowchart illustrating an exemplary process for determining a DOM profile based on a 3D image according to some embodiments of the present disclosure.

In 1110, the obtaining unit 1010 may obtain a 3D image of an object. In some embodiments, the obtaining unit 610 may obtain the 3D image of the object from a storage device (e.g., the storage 150, the disk 270, the memory 360, the storage module 430, an external storage device). In some embodiments, the obtaining unit 1010 may obtain the 3D image of the object from an imaging device (e.g., a 3D depth camera).

In some embodiments, the 3D image may be taken by a 3D depth camera. A 3D contour of an object may be estimated based on the 3D image. The 3D depth camera may generate the 3D image based on a stereoscopic vision technology, a structured light technology, a Time-of-Flight (ToF) technology, or the like, or any combination thereof. In some embodiments, the 3D depth camera may take the 3D image of the object from multiple angles including but not limited to from the front, from the bottom, from a side, etc.

In 1120, the 3D contour determination unit 1020 may determine a 3D contour of the object based on the 3D image. The 3D image may include pixels. A pixel in the 3D image may contain information relating to a corresponding point on the object. For instance, a pixel in the 3D image may contain information relating to the distance from the 3D depth camera to a corresponding point on the object, the greyscale value or color of the corresponding point on the object, or the like, or a combination thereof. The distance information of pixels in the 3D image may be used to provide a 3D contour of the object. In some embodiments, the 3D contour may include a cylinder, an elliptic cylinder, a cuboid, or the like. The 3D contour may include information of the surface structure or shape of the object, such as width, thickness, or the like, or any combination thereof. In some embodiments, a topogram image may be used to estimate the 3D contour of an object. For example, the 3D contour of the object may be estimated based on attenuation data of the object in the topogram image. However, as the topogram image is a 2D image that corresponds to a fixed scan angle (usually vertically downwards), shape or size of the object, especially in the lateral and oblique directions, cannot be accurately estimated. In order to solve this problem, a 3D image may be used to generate a more accurate shape or 3D contour of the object. It should be noted that even though 3D images may show slight advantage over topogram images in certain scenarios, determining the 3D contour based on the topogram image solely or collectively with the 3D image is also within the protection scope of the present disclosure.

In 1130, the DOM profile generation unit 1030 may determine a radiation dose corresponding to each slice of the object based the 3D contour of the object. For example, the object may be divided to a plurality of slices along the Z-axis. The plurality of slices may be parallel to each other. In some embodiments, a slice may correspond to a particular time during a scan and a particular scanning angle. For each slice of the object, the shape of the slice (e.g., thickness, width, length) may be determined based on the 3D contour of the object. For example, if the 3D contour of the object is an elliptic cylinder, each slice may be an ellipse. The size or one or more other parameters of an elliptical slice may be determined based on the 3D contour of the object.

In some embodiments, a radiation dose corresponding to each slice may be determined based on the shape of the slice. For example, a mapping table including a relationship between radiation doses and sizes (e.g., thickness) of slices may be predetermined and may be stored in a storage device (e.g., the storage 150, the disk 270, the memory 360, the storage module 430, an external storage device). The DOM profile generation unit 1030 may search the mapping table and determine the radiation doses corresponding to each of the plurality of slices based on the shape of the slice.

In 1140, the DOM profile generation unit 1030 may generate a DOM profile based on the plurality of radiation doses corresponding a plurality of slices of the object. After the DOM profile generation unit 1030 determine the plurality of radiation doses of the plurality of slices, the DOM profile generation unit 1030 may arrange the plurality of radiation doses determined in an order of the scanning angle (or a direction of the Z-axis) to generate a DOM profile. The DOM profile may be used as a reference in performing the radiation dose modulation by way of, e.g., adjusting tube current of the radioactive scanning source 113 during a CT scan. In some embodiments, the DOM profile may be a continuous curve indicating a continuous change of the radiation dose over time or angle. In some embodiments, the DOM profile may include one or more discrete points each of which corresponds to a radiation dose at a specific time or angle. In some embodiments, the DOM profile may include a combination of one or more sections of continuous curves, or a combination of one or more sections of continuous curves and one or more discrete points.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, operations 1130 and 1140 may be combined into one operation.

Figure 12:
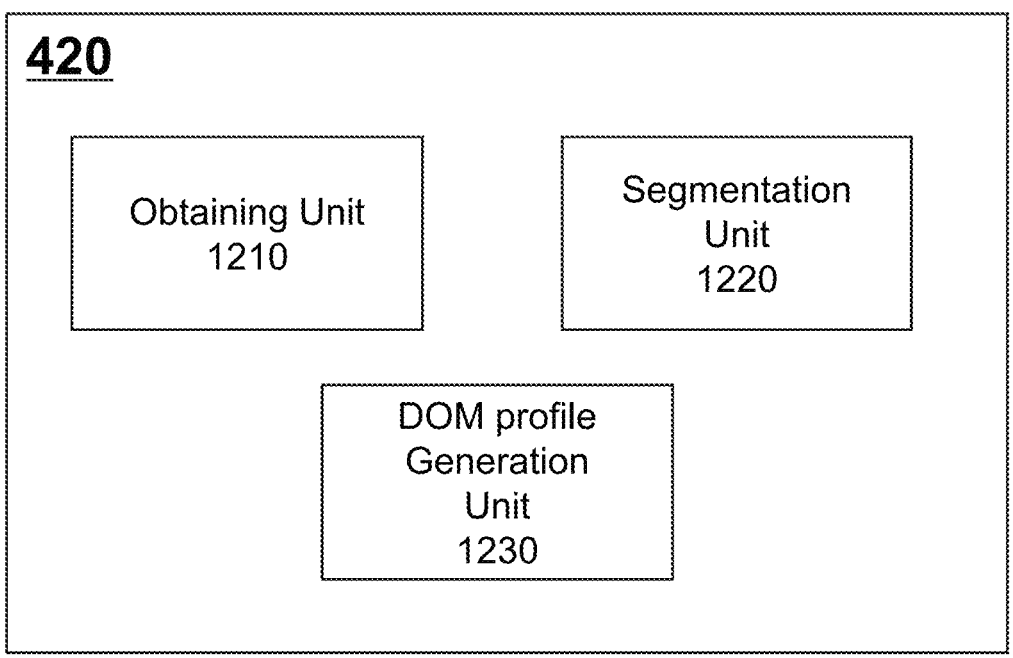
FIG. 12 is a schematic block diagram illustrating an exemplary processing module according to some embodiments of the present disclosure.

FIG. 12 is a schematic block diagram illustrating an exemplary processing module according to some embodiments of the present disclosure. The processing module 420 may include an obtaining unit 1210, a segmentation unit 1220, and a DOM profile generation unit 1230.

The obtaining unit 1210 may be configured to obtain a topogram image of an object. In some embodiments, the obtaining unit 1210 may obtain the topogram image of the object from a storage device (e.g., the storage 150, the disk 270, the memory 360, the storage module 430, an external storage device). In some embodiments, the obtaining unit 1210 may obtain the topogram image of the object from an imaging device (e.g., a CT scanner, a PET-CT scanner). In some embodiments, the topogram image may be an AP topogram image or a lateral topogram image. In some embodiments, the obtaining unit 610 may obtain both an AP topogram image and a lateral topogram image of the object.

In some embodiments, the obtaining unit 1210 may be configured to obtain a reference 3D image. In some embodiments, the reference 3D image may be associated with the object that is scanned. For example, the reference 3D image may be a recent image of a reference object that is the same as or similar to the scanned object (e.g., the same type or region). More particularly, the reference object and the scanned object may have the same or similar physical conditions, such as a same or similar shape of 3D contour, a same tissue or organ inside, or the like, or any combination thereof.

The segmentation unit 1220 may be configured to segment a topogram image of an object into a plurality of regions. Each of the plurality of regions may correspond to an anatomical region of the object such as the head, the neck, the chest, or the like. In some embodiments, the segmentation unit 1220 may automatically segment the topogram image into the plurality of regions based on an image segmentation algorithm. Exemplary image segmentation algorithms may include a thresholding algorithm, a clustering algorithm, a histogram-based algorithm, a region-growing algorithm, or the like, or any combination thereof. In some embodiments, an operator (e.g., a nurse, a radiologist) may manually segment the topogram image into the plurality of regions. In some embodiments, the topogram image may be segmented semi-automatically by the segmentation unit 1220 with input from an operator.

The DOM profile generation unit 1230 may be configured to generate a DOM profile. The DOM profile generation unit 1230 may determine a plurality of reference topogram images corresponding to the plurality of regions and may determine a plurality of regional DOM profiles based on the plurality of reference topogram images. The DOM profile generation unit 1230 may further combine the plurality of regional DOM profiles to generate a DOM profile. An exemplary DOM profile may be found in e.g., FIG. 15.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, one or more units in the processing module 420 may each include an independent storage unit.

Figure 13:
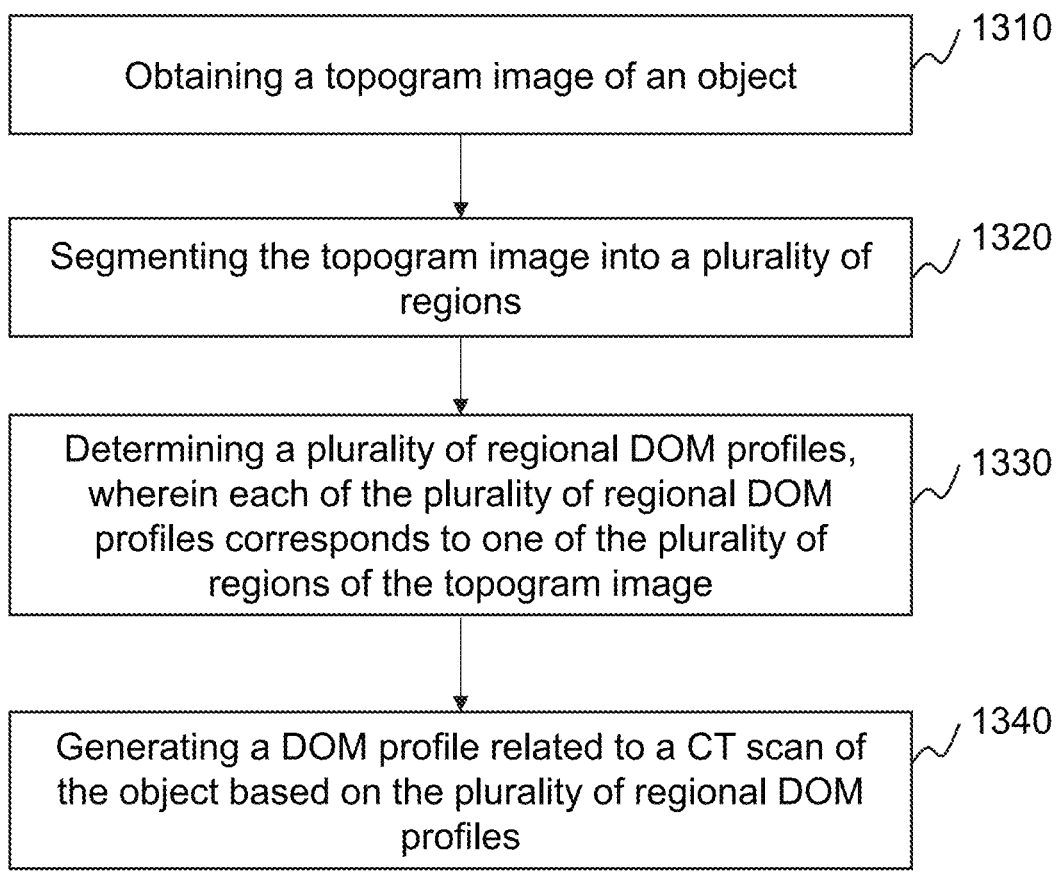
FIG. 13 is a flowchart illustrating an exemplary process for determining a DOM profile based on a topogram image according to some embodiments of the present disclosure.

FIG. 13 is a flowchart illustrating an exemplary process for determining a DOM profile based on a topogram image according to some embodiments of the present disclosure.

In 1310, the obtaining unit 1210 may obtain a topogram image of an object. The obtaining unit 1210 may obtain the topogram image of the object from a storage device (e.g., the storage 150, the disk 270, the memory 360, the storage module 430, an external storage device). In some embodiments, the topogram image may be an AP topogram image or a lateral topogram image. In some embodiments, the obtaining unit 1210 may obtain both an AP topogram image and a lateral topogram image of the object in operation 1310.

In some embodiments, the topogram image may include attenuation data of the object. The attenuation data in the topogram image may be used to estimate attenuation characteristics of the object. The attenuation characteristics of the object may relate to radiation dose modulation in performing a CT scan on the object. For example, a hard tissue (e.g., a bone), identified as a brighter region in a topogram image, may have a higher attenuation coefficient and need a higher radiation dose (corresponding to a higher tube current) during a CT scan than a soft tissue (e.g., lungs), identified as a darker region in the topogram image.

In 1320, the segmentation unit 1220 may segment the topogram image of an object into a plurality of regions. Each of the plurality of regions may correspond to an anatomical region of the object such as the head, the neck, the chest, or the like. In some embodiments, the segmentation unit 1220 may automatically segment the topogram image into the plurality of regions based on an image segmentation algorithm. Exemplary image segmentation algorithms may include a thresholding algorithm, a clustering algorithm, a histogram-based algorithm, a region-growing algorithm, or the like, or any combination thereof. In some embodiments, an operator (e.g., a nurse, a radiologist) may manually segment the topogram image into the plurality of regions. In some embodiments, the topogram image may be segmented semi-automatically by the segmentation unit 1220 with input from an operator.

In 1330, the DOM profile generation unit 1230 may determine a plurality of regional DOM profiles. Each of the plurality of regional DOM profiles may correspond to one of the plurality of regions of the topogram image. In some embodiments, the DOM profile or a regional DOM profile may be a continuous curve indicating a continuous change of the radiation dose over time or angle. In some embodiments, the DOM profile or a regional DOM profile may include one or more discrete points each of which corresponds to a radiation dose at a specific time or angle. In some embodiments, the DOM profile or a regional DOM profile may include a combination of one or more sections of continuous curves, or a combination of one or more sections of continuous curves and one or more discrete points. The detailed description regarding the determination of the plurality of regional DOM profile may be found elsewhere in the present disclosure (e.g., FIG. 14 and the descriptions thereof).

In 1340, the DOM profile generation unit 1230 may generate a DOM profile related to a CT scan of the object based on the plurality of regional DOM profiles. After the plurality of regional DOM profiles are determined in operation 1320, the DOM profile generation unit 1230 may combine the plurality of regional DOM profiles to generate the DOM profile. In some embodiments, a smoothing process may be performed on the generated DOM profile to avoid sudden change of radiation doses in the edges of the regional DOM profiles.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, two topogram images (e.g., an AP topogram image and a lateral topogram image) may be obtained in operation 1310. In some embodiments, an original scan protocol may be set before the operation 1310. The original scan protocol may be set manually by an operator (e.g., a nurse, a radiologist), or automatically by the imaging system 100. The obtaining unit 1210 may obtain a topogram image of an object based on the original scan protocol, and the DOM profile generation unit 1230 may further determine an original DOM profile based on the topogram image and the original scan protocol. After a reference DOM profile is determined based on operations 1310-1340 described above, the original DOM profile and the reference DOM profile may be compared. If the difference between the original DOM profile and the reference DOM profile is greater than a preset threshold, the imaging system 100 may remind an operator (e.g., a nurse, a radiologist) that the original scan protocol is inaccurate. For example, the imaging system 100 may generate an audio reminder and/or display a visual reminder on an operating interface (e.g., a graphic user interface (GUI) of the terminal 130) to remind the operator. In some embodiments, the original scan protocol may be calibrated manually by the operator or automatically by the imaging system 100 based on the comparison result. For example, the imaging system 100 may automatically calibrate the original scan protocol and display a result of the calibration on the operating interface to be further verified by the operator. As another example, the operator may revise the original scan protocol via the operating interface manually.

Figure 14:
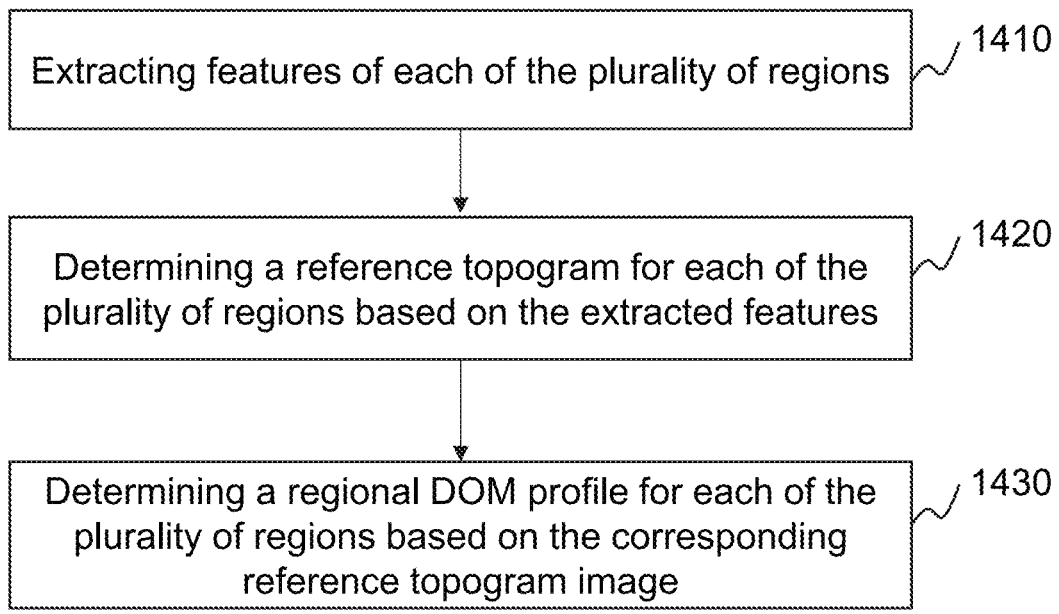
FIG. 14 is a flowchart illustrating an exemplary process for determining a regional DOM profile according to some embodiments of the present disclosure.

FIG. 14 is a flowchart illustrating an exemplary process for determining a regional DOM profile according to some embodiments of the present disclosure.

In 1410, the DOM profile generation unit 1230 may extract features of each of the plurality of regions of the topogram of the object. The features of a region may include a textural feature, the shape, a spatial feature, or the like, or any combination thereof. In some embodiments, different regions of the topogram of the object may have different features. In some embodiments, the DOM profile generation unit 1230 may extract the features of each of the plurality of regions based on a feature extraction technique. The textural feature may be extracted according to a textural feature extraction technique such as a spatial texture feature extraction technique and a spectral texture feature extraction technique. The shape may be determined according to a technique such as a contour-based technique and a region-based technique. The spatial feature may be extracted according to a spatial feature extraction technique such as an absolute spatial location-based technique and a relative spatial location-based technique.

In 1420, the DOM profile generation unit 1230 may determine a reference topogram image for each of the plurality of regions based on the extracted features. Based on the extracted features obtained in operation 1410, each of the plurality of regions may be represented by a feature vector. In some embodiments, a plurality of candidate topogram images may be stored in a storage device (e.g., the storage 150, the disk 270, the memory 360, the storage module 430, an external storage device) and each of the plurality of candidate topogram images may be represented by a feature vector. If a feature vector of a candidate topogram image of a region matches the feature vector of one of the plurality of regions to an acceptable degree, the candidate topogram image may be designated as the reference topogram image that corresponds to the region. Merely by way of example, a topogram image of the chest of the object may correspond to a first feature vector. The plurality of candidate topogram images may correspond to a plurality of regions including a head, a chest, a neck, an abdomen, a pelvis, a leg, etc. In some embodiments, a reference image that has a second feature vector matching the first feature vector of the chest of the topogram image of the object may be selected from the plurality of candidate topogram images. The reference image may include a chest similar to the chest in the topogram image. As used herein, that a candidate topogram image matches a region to an acceptable degree may indicate that the difference between the candidate topogram image and the region is below a threshold. The difference may be assessed with respect to one or more features of the feature vector of the candidate topogram image and the region.

In 1430, the DOM profile generation unit 1230 may determine a regional DOM profile for each of the plurality of regions based on the corresponding reference topogram image. The corresponding reference topogram image may be associated with a scan protocol such as a head scan protocol, a neck scan protocol, a chest scan protocol, or the like. In some embodiments, the scan protocol may include scan parameters such as the voltage of the radioactive scanning source 113, a tube current-time product, a beam width, gantry rotation time, reconstruction kernel, or the like, or any combination thereof. Different scan protocols may have the same or different scan parameters. For instance, different scan protocols may have some scan parameters that are the same and some scan parameters that are different. The DOM profile generation unit 1230 may determine the regional DOM profile for each of the plurality of regions based on one or more scan parameters of the scan protocol associated with the corresponding reference topogram image. In some embodiments, for each of the plurality of regions, the DOM profile generation unit 1230 may further obtain one or more image parameters (e.g., the greyscale values of pixels, the average greyscale value, the contrast) of the region in the topogram image of the object and determine the regional DOM profile for the region based on the one or more image parameters of the region and the one or more scan parameters of the scan protocol associated with the corresponding reference topogram image.

In some embodiments, the DOM profile generation unit 1230 may determine a regional DOM profile for each of the plurality of regions based on a DOM profile generation model (see, e.g., FIG. 7 and the descriptions thereof). As used herein, the corresponding reference topogram image determined in operation 1420 and/or a reference 3D image (e.g., obtained as described in connection with obtaining unit 610) may be designated as an input to the DOM profile generation model. The DOM profile generation model may generate the regional DOM profile for each of the plurality of regions based on the corresponding reference topogram image and the reference 3D image.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1430 may be divided into a set of sub-operations. The DOM profile generation unit 1230 may determine a scan protocol associated with the reference topogram image in a sub-operation and generate a regional DOM profile based on one or more parameters of the scan protocol in another sub-operation. As another example, operation 1430 may be divided into a different set of sub-operations. The DOM profile generation unit 1230 may obtain a DOM profile generation model and a reference 3D image in a first sub-operation, and generate a regional DOM profile based the DOM profile generation model, the reference 3D image, and the reference topogram image in a second sub-operation.

Figure 15:
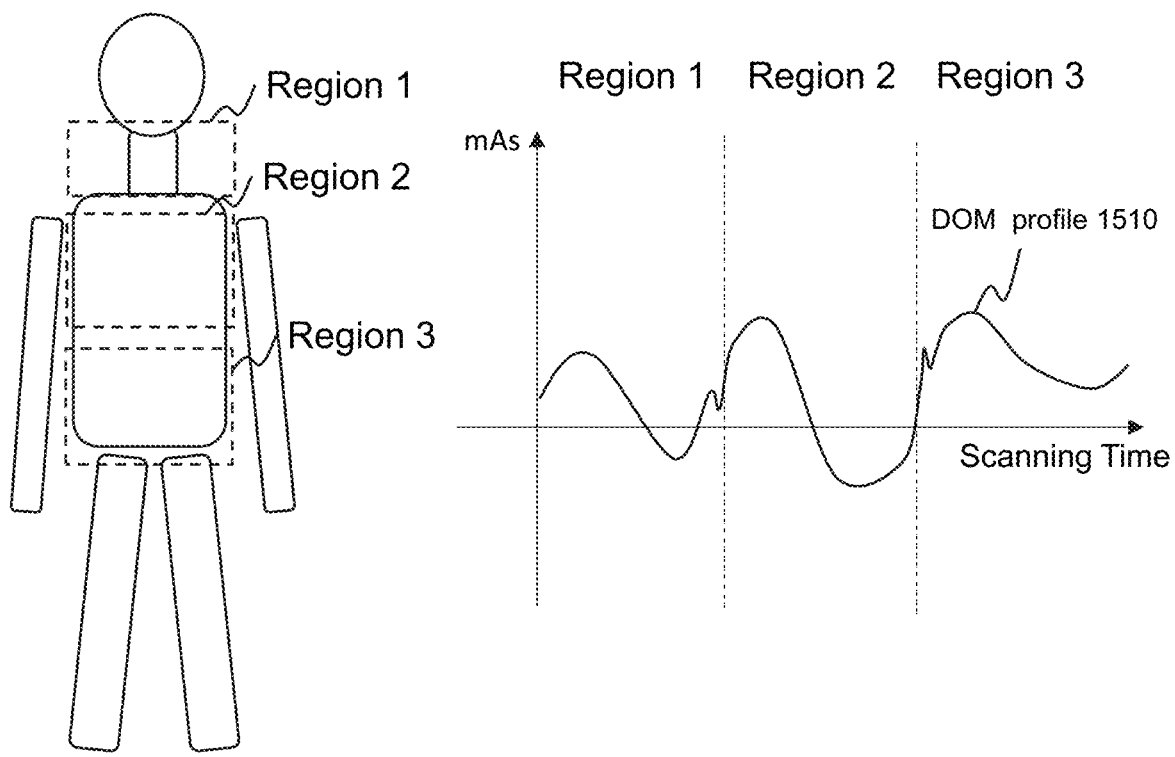
FIG. 15 is a schematic diagram illustrating an exemplary human body and an exemplary DOM profile determined according to some embodiments of the present disclosure.

FIG. 15 is a schematic diagram illustrating an exemplary human body and an exemplary DOM profile determined according to some embodiments of the present disclosure.

As shown in FIG. 15, the scanning device 110 may perform a whole-body CT scan on a patient. The whole-body CT scan may include scanning the neck, the chest, and the abdomen and pelvis of the patient. The scanning device 110 may first take a 3D image of the patient using the 3D depth camera 112 and may then perform a localizer scan on the patient to generate a topogram image.

In some embodiments, the processing device 140 may segment the topogram image into three regions: the neck (Region 1), the chest (Region 2), and the abdomen and pelvis (Region 3). The processing device 140 may determine three reference topogram images: a neck-related reference topogram image, a chest-related reference topogram image, and an abdomen-pelvis-related reference topogram image. For each region, the processing device 140 may determine a regional DOM profile based on the reference topogram image associated with the region. For example, the processing device 140 may determine the neck-related regional DOM profile based on one or more scan parameters of a scan protocol associated with the neck-related reference topogram image. As another example, the processing device 140 may determine the neck-related regional DOM profile by input the neck-related reference topogram image and the 3D image of the patient to a DOM profile generation model. After obtaining the neck-related regional DOM profile, the chest-related regional DOM profile, and the abdomen-pelvis-related regional DOM profile, the processing device 140 may combine the regional DOM profiles to generate a DOM profile 1510. In some embodiments, a smoothing process may be performed on the generated DOM profile to avoid sudden change of radiation doses in the edges of the regional DOM profiles.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For instance, more than three (e.g., four, five) regional DOM profiles may be determined and then combined to generate a corresponding DOM profile. As another example, rather than curves, the DOM profile and/or the regional DOM profiles may include one or more discrete points each of which corresponds to a radiation dose at a specific time or angle.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a specific feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the specific features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method implemented on a computing device including a processor and a storage medium for determining a dose of modulation (DOM) profile, the method comprising:
    obtaining a 3D image of an object;
    determining a 3D contour of the object based on the 3D image;
    dividing the object into a plurality of slices;
    for each slice of the plurality of slices of the object,
        determining a size of the each slice of the object based on the 3D contour of the object,
        obtaining a relationship between X-ray doses and sizes of slices, and
        determining an X-ray dose corresponding to the each slice of the object by searching the relationship based solely on the size of the each slice; and
    generating a dose of modulation (DOM) profile based on a plurality of X-ray doses corresponding to the plurality of slices of the object.

2. The method of claim 1, wherein the determining a 3D contour of the object based on the 3D image comprises:
    generating a preliminary 3D contour;
    determining a plurality of parameters of the preliminary 3D contour based on the 3D image of the object; and
    updating the preliminary 3D contour based on the plurality of parameters to generate the 3D contour of the object.

3. A method implemented on a computing device including a processor and a storage medium for determining a dose of modulation (DOM) profile, the method comprising:
    obtaining a topogram image of an object;
    segmenting the topogram image into a plurality of regions;
    extracting features of each of the plurality of regions;
    obtaining a plurality of candidate topogram images;

determining a reference topogram image from the plurality of candidate topogram image for each of the plurality of regions based on the extracted features;

determining a regional DOM profile for each of the plurality of regions based on the corresponding reference topogram image;

determining a plurality of regional dose of modulation (DOM) profiles, wherein each of the plurality of regional DOM profiles corresponds to one of the plurality of regions of the topogram image; and generating a DOM profile related to a computed tomography (CT) scan of the object based on the plurality of regional DOM profiles.

4. The method of claim 3, wherein the determining a regional DOM profile for each of the plurality of regions based on the corresponding reference topogram image further comprises:

for the each of the plurality of regions,
obtaining a scan protocol associated with the corresponding reference topogram image; and
determining the regional DOM profile related to the each of the plurality of regions based on one or more parameters of the scan protocol associated with the corresponding reference topogram image.

5. The method of claim 3, wherein the determining the regional DOM profile related to the each of the plurality of regions based on one or more parameters of the scan protocol associated with the corresponding reference topogram image further comprises:

for the each of the plurality of regions,
obtaining a scan protocol associated with the corresponding reference topogram image;
obtaining one or more image parameters of the region in the topogram image of the object; and
determining the regional DOM profile related to the each of the plurality of regions based on the one or more image parameters of the region and the one or more parameters of the scan protocol associated with the corresponding reference topogram image.

6. The method of claim 3, wherein the determining a regional DOM profile for each of the plurality of regions based on the corresponding reference topogram image further comprises:

for the each of the plurality of regions,
obtaining a reference 3D image corresponding to the reference topogram image;
obtaining a DOM profile generation model; and
executing the DOM profile generation model to generate the regional DOM profile based on the reference 3D image and the reference topogram image.

7. The method of claim 6, wherein the DOM profile generation model is generated by a process comprising:

obtaining a preliminary model;
obtaining a set of training data including
a plurality of sample CT images,
a plurality of sample 3D images corresponding to the plurality of sample CT images, respectively, and
a plurality of sample topogram images corresponding to the plurality of sample CT images, respectively; and
training the preliminary model based on the set of training data to generate the DOM profile generation model.

8. The method of claim 7, wherein the training the preliminary model based on the set of training data to generate the DOM profile generation model comprises:

determining a plurality of sample DOM profiles based on the plurality of sample CT images;
executing the preliminary model based on the plurality of corresponding sample 3D images and the plurality of corresponding sample topogram images to generate a plurality of predicted DOM profiles; and
training the preliminary model by minimizing an average difference between the plurality of predicted DOM profiles and the plurality of sample DOM profiles.

9. The method of claim 6, wherein the DOM profile generation model includes a neural network model.

* * * * *